(12) United States Patent
Amthor et al.

(10) Patent No.: US 10,245,447 B2
(45) Date of Patent: Apr. 2, 2019

(54) MAGNETIC RESONANCE IMAGING GUIDED BRACHYTHERAPY WITH DISPLAYING THE CATHETER PLACEMENT POSITION

(71) Applicant: KONINKLIJKE PHILIPS N.V., Eindhoven (NL)

(72) Inventors: Thomas Erik Amthor, Hamburg (DE); Falk Uhlemann, Hamburg (DE); Sascha Krueger, Hamburg (DE); Steffen Weiss, Hamburg (DE); Ronaldus Frederik Johannes Holthuizen, Best (NL); Daniel Wirtz, Hamburg (DE); Peter Koken, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 782 days.

(21) Appl. No.: 14/349,333

(22) PCT Filed: Sep. 25, 2012

(86) PCT No.: PCT/IB2012/055093
§ 371 (c)(1),
(2) Date: Apr. 3, 2014

(87) PCT Pub. No.: WO2013/057609
PCT Pub. Date: Apr. 25, 2013

(65) Prior Publication Data
US 2014/0303423 A1 Oct. 9, 2014

Related U.S. Application Data

(60) Provisional application No. 61/548,356, filed on Oct. 18, 2011.

(51) Int. Cl.
*A61N 5/10* (2006.01)

(52) U.S. Cl.
CPC ......... *A61N 5/1007* (2013.01); *A61N 5/1027* (2013.01); *A61N 5/1039* (2013.01);
(Continued)

(58) Field of Classification Search
CPC .... A61B 5/055; A61N 5/1007; A61N 5/1039; A61N 5/1027; A61N 5/1064; A61N 2005/1055; A61N 2005/1024
See application file for complete search history.

(56) References Cited

U.S. PATENT DOCUMENTS 5,391,139 A * 2/1995 Edmundson ........... A61N 5/103
                                                              600/3
6,200,255 B1    3/2001 Yu
(Continued)

OTHER PUBLICATIONS

O.M. Al-Bataineh, et al., "Utilization of the High-Frequency Piezo-electric Ceramic Hollow Spheres for Exposimetry and Tissue Ablation", Proceedings of the IEEE 2002 Ultrasonics Symposium, Munich, Germany, Oct. 8-11, 2002, Secession P3C-7, 4 pages total.
(Continued)

Primary Examiner — Serkan Akar

(57) ABSTRACT

The invention provides for a medical apparatus (200, 300, 400) comprising: a magnetic resonance imaging system (202), a display (270), a processor (228), and a memory (234) for storing instructions for the processor. The instructions causes the processor to receive a brachytherapy treatment plan (240), acquire (100) planning magnetic resonance data (244), calculate (102) a catheter placement positions (246, 900, 902) and a catheter control commands (248) the brachytherapy catheters. The instructions cause the processor, for each catheter placement position, to repeatedly: acquire (106) guidance magnetic resonance data (250), reconstruct (108) an image (252, 500), display (110) the
(Continued)

image and the catheter placement position on the display, receive (114) a catheter inserted signal from a user interface, segment (116) the image to determine the catheter placement position after receiving the catheter inserted signal, recalculate (116) the catheter placement positions for each remaining catheter placement position after receiving the catheter inserted signal, and recalculate (116) the catheter control command for all of the multiple catheters after receiving the catheter inserted signal.

15 Claims, 16 Drawing Sheets

(52) U.S. Cl.
CPC .... *A61N 5/1064* (2013.01); *A61N 2005/1024* (2013.01); *A61N 2005/1055* (2013.01)

(56) References Cited

U.S. PATENT DOCUMENTS

| | | | |
|---|---|---|---|
| 6,217,518 B1* | 4/2001 | Holdaway | A61B 5/6848 600/439 |
| 6,311,084 B1 | 10/2001 | Cormack et al. | |
| 6,438,401 B1* | 8/2002 | Cheng | A61B 8/0833 128/898 |
| 6,482,142 B1 | 11/2002 | Winkler et al. | |
| 6,666,812 B2 | 12/2003 | Jahrmarkt et al. | |
| 6,846,282 B1* | 1/2005 | Ford | A61N 5/1007 600/1 |
| 7,517,310 B2 | 4/2009 | Lubock et al. | |
| 7,686,755 B2 | 3/2010 | Smith | |
| 7,762,940 B2 | 7/2010 | Henderson et al. | |
| 7,881,770 B2 | 2/2011 | Melkent et al. | |
| 2003/0233123 A1* | 12/2003 | Kindlein | A61N 5/1031 607/2 |
| 2010/0056900 A1* | 3/2010 | Whitcomb | A61B 5/055 600/414 |
| 2011/0077504 A1* | 3/2011 | Fischer | A61B 19/2203 600/411 |
| 2011/0201931 A1* | 8/2011 | Palmeri | A61B 8/0841 600/440 |

OTHER PUBLICATIONS

R. Alterovitz, et al., "Optimization of HDR Brachytherapy Dose Distributions Using Linear Programming with Penalty Costs", Med. Phys. 33 (1), Nov. 2006, pp. 4012-4019.

D.J. Brenner, et al., "Conditions for the Equivalence of Continuous to Pulsed Low Dose Rate Brachytheraphy", Int. J. Radiation Oncology; Biol. Phys. vol. 20, Sep. 12, 1990, pp. 181-190.

F. Fischbach, et al., "MR-Guided Freehand Biopsy of Liver Lesions With Fast Continuous Imaging Using a 1.0-T Open MRI Scanner: Experience in 50 Patients", Cardiovasc Intervent Radiol (2011) vol. 34, pp. 188-192.

E. Lessard, et al., "Inverse Planning Anatomy-Based Dose Optimization for HDR-Brachytherapy of the Prostate using Fast Simulated Annealing Algorithm and Dedicated Objective Function", Med. Phys. 28 (5), May 2001, pp. 773-779.

J. Ricke, et al., "MR-Guided Liver tumor Ablation Employing Open High-Field 1.0T MRI for Image-Guided Brachtherapy", Eur Radiol, Published Online Mar. 20, 2010, 9 pages total.

M.J. Rivard, et al., "Update of AAPM Task Group No. 43 Report: A Revised AAPM Protocol for Brachytherapy Dose Calculations", Med. Phys. 31 (3), Mar. 2004, pp. 633-674.

K. Ulin, et al., "A Technique for Accurate Planning of Stereotactic Brain Implants Prior to Head Ring Fixation", Int. J. Radiation Oncology Biol. Phys., vol. 39, No. 3, May 19, 1997, pp. 757-767.

Nath, R. et al. "Development of an 241Am applicator for intracavitary irradiation of gynecologic cancers", Int J Radial Oncol Biol Phys. May 1988; 14(5): 969-78.

Menard, C. et al., "MRI-Guided HDR prostate brachytherapy in standard 1.5T scanner", Int J Radial Oncol Biol Phys, Aug. 1, 2004; 59(5): 1414-1423.

* cited by examiner

MAGNETIC RESONANCE IMAGING GUIDED BRACHYTHERAPY WITH DISPLAYING THE CATHETER PLACEMENT POSITION

CROSS-REFERENCE TO PRIOR APPLICATIONS

This application is the U.S. National Phase application under 35 U.S.C. § 371 of International Application Serial No. PCT/IB2012/055093, filed on Sep. 25, 2012, which claims the benefit of U.S. Application Ser. No. 61/548,356, filed on Oct. 18, 2011. These applications are hereby incorporated by reference herein.

TECHNICAL FIELD

The invention relates to brachytherapy, in particular it relates to magnetic resonance guided brachytherapy.

BACKGROUND OF THE INVENTION

High dose rate (HDR) brachytherapy is a very promising method for treating different kinds of tumors. One or more catheters are inserted directly into one or several tumor(s) in a minimally invasive procedure. Through these catheters, small radioactive seeds can be shifted to pre-defined positions in order to deposit a high radiation dose precisely in the lesion with only minimal damage of surrounding healthy tissue compared to other focal techniques. At the same time HDR brachytherapy allows treatment of larger tumors and is unlike Radio-Frequency Ablation (RFA) not prone to cooling effects of nearby vessels. HDR brachytherapy allows accurate focal treatment in deformable or even moving tissue.

Current treatment planning software optimizes the dose distribution after the intervention, when the catheters are already placed in the patient and the positions are fixed. The parameters which can then be varied are the dwell positions and the dwell times of the radioactive seed being shifted through the catheters.

Besides time-consuming graphical interactive optimization algorithms, where these parameters are set manually, a forward calculation of the dose distribution is performed to check if all constraints are fulfilled, very efficient inverse planning algorithms have been developed which are able to find the optimal distribution of dwell times and positions in less than a minute.

While catheter placement is conventionally performed under ultrasound guidance or using guiding templates fixed to the patient, new real-time MR-guided techniques offer a much higher functional specificity and spatial precision. With the development of MR-guided interventional procedures, ways of further optimization of the treatment open up.

SUMMARY OF THE INVENTION

The invention provides for a medical apparatus, a method of using the medical apparatus and a computer program product in the independent claims. Embodiments are given in the dependent claims.

A disadvantage of current methods of guiding brachytherapy catheters is that it is very difficult for a physician to place the catheter in exactly the correction position. Catheter placement and the location of radioactive sources within the catheters as a function of time can be calculated before catheter placement, but it is very likely that after the catheters have been placed that the resulting treatment plan will be incorrect.

Embodiments of the invention may solve this problem and others by using magnetic resonance imaging to provide images useful for guidance for catheter placement. After a catheter is placed embodiments of the invention may determine the location of placed catheters using a magnetic resonance image. The location of the placed catheters is then used an input for a calculation where the placement of the remaining catheters is determined. This provides a means of compensating for catheters which have been placed incorrectly or a wrong location.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, punched tape, punch cards, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. the memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, one or more switches, one or more buttons, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical apparatus. The medical apparatus comprises a magnetic resonance imaging system for acquiring magnetic resonance data from an imaging zone. The imaging zone is a region within the magnetic field generated by the magnetic resonance imaging system where the magnetic field is strong and uniform enough for performing magnetic resonance imaging. The medical apparatus further comprises a display for displaying images such as an image generated by a magnetic resonance imaging system. The medical apparatus further comprises a processor for controlling the medical apparatus. The medical apparatus further comprises a memory for storing machine executable instructions for execution by the processor. Execution of the instructions causes the process to receive a brachytherapy treatment plan for treating a subject. The brachytherapy treatment plan may identify such things as the region of the subject to be treated along with the amount of radiation that the treatment region should be subjected to. The brachytherapy treatment plan may also outline regions of anatomy which may be damaged by excessive radiation. In some embodiments the brachytherapy treatment plan also contains or details pathways within the subject which are suitable for passing a catheter through.

Execution of the instructions further causes the processor to acquire planning magnetic resonance data using the magnetic resonance imaging system. The planning magnetic resonance data is magnetic resonance data which is used for planning the placement of the catheters. Execution of the instructions further causes the processor to calculate a catheter placement position and a catheter control command for each of the multiple brachytherapy catheters using the brachytherapy treatment plan and the planning magnetic resonance data. This is essentially an optimization step where the processor empirically places different catheters within the subject or model of the subject and tries to optimize the catheter placement and commands for controlling the catheter to optimize the therapy. A catheter placement position may be a location or intended location of a catheter to be placed.

A catheter control command is a command or set of instructions which detail a time and a position a brachytherapy radiation source should be in place during treatment of the subject. The catheter control command may for instance be executed by an automated system or performed by a physician. Once a catheter placement has been planned using the planning magnetic resonance data and the brachytherapy treatment plan the magnetic resonance imaging system is then used to provide data which a physician may use for guiding the actual catheter placement. For each catheter placement position guidance magnetic resonance data is acquired repeatedly. Guidance magnetic resonance data is magnetic resonance data that is acquired periodically or repeatedly to show the location or determine the location of a catheter as it is being placed into the subject.

Execution of the instructions further causes the processor to repeatedly reconstruct an image from the guidance magnetic resonance data. Execution of the instructions further causes the processor to repeatedly display the image on the display. Execution of the instructions also causes the processor to repeatedly display the catheter placement position on the image. This is beneficial because a physician may use the repeatedly updated image on the display for the guidance of the catheter. After the catheter has been placed execution of the instructions cause the processor to receive a catheter inserted signal from the user interface. For instance after a physician has suitably placed a catheter he or she may hit an instruction or a command on the user interface to indicate that the catheter has been placed.

Execution of the instructions further cause the processor to repeatedly segment the image to determine the catheter placement position after receiving the catheter inserted signal. The segmentation of the image allows the accurate determination of exactly where the catheter is within the person. Execution of the instructions further cause the processor to repeatedly recalculate the catheter placement for each remaining catheter placement position after receiving the catheter inserted signal. After a catheter has been placed the catheter may not be in exactly the desired position. For this reason after the catheter has been placed each catheter placement position and catheter control commands are recalculated. The catheter control commands are recalculated also because both the location of the radiation source and its position as a function of time is necessary to calculate the dose to the treatment zone and also to surrounding tissue which is not desired to be eradiated during the brachytherapy treatment. Essentially both the catheter placement for each remaining catheter placement position is to be calculated after receiving the catheter inserted signal and the catheter control command for all of the multiple catheters are recalculated after receiving the catheter inserted signal.

This embodiment may have the benefit that as catheters are placed it may not be possible for the physician to place the catheter exactly at a catheter placement position. The magnetic resonance data is used to determine the actual location of where the catheter is placed and then to compensate by adjusting the catheter control commands and/or the catheter placements for the catheters that still need to be placed into the subject.

In another embodiment at least one of the multiple brachytherapy catheters is configured for generating an anisotropic radiation field. The catheter control command is further descriptive of a rotational position of the anisotropic radiation field of the radiotherapy catheter for each of the dwell times. Essentially a catheter may be created which does not generate radiation equally in all different directions. This may be particularly beneficial because an area which is desired to be treated may be adjacent to a sensitive organ which it is not desirable to expose to radiation. The catheter control commands further comprise rotational instructions which indicate how the brachytherapy catheter should be inserted and rotated to ensure that the radiation is direction in the desirable direction.

In another embodiment the medical apparatus further comprises a catheter actuator configured for controlling the position and/or the rotational position of the anisotropic radiation field of each of the multiple brachytherapy catheters as a function of time. Execution of the instructions further causes the processor to control the position of the multiple brachytherapy catheters as a function of time with the catheter actuator in accordance with the catheter control commands. This embodiment is beneficial because once the catheters are inserted within the subject the catheter actuators may be used for automatically executing and controlling the position of the brachytherapy catheters as a function of time. This may enable more precise brachytherapy of a treatment region.

In another embodiment the at least one of the multiple brachytherapy catheters comprises an anisotropic radiation source for generating the anisotropic radiation field with a radial and/or axial symmetry. For instance a bead or a portion of a radiation source may be asymmetric or it may be unequally shielded within the catheter. For instance one part of the anisotropic radiation source may have radiation shielding which causes the anisotropic radiation field.

In another embodiment the at least one brachytherapy catheter comprises a magnetic resonance positional marker descriptive of the rotational position of the anisotropic radiation field. For instance a resonant circuit which shows up on the magnetic resonance data may be included in the brachytherapy catheter or a high contrast agent such as fluorine or other source may be included at the tip. The rotational position of the circuit may be determined by having the antenna of the resonant circuit perpendicular to the rotation so that the signal changes as the source is rotated. If a high contrast agent is contained within a small container at the tip of the catheter this container may have a shape which is recognizable and indicative of its position when viewed in a magnetic resonance image.

Execution of the instructions further cause the processor to determine a current rotational position of the anisotropic radiation field by identifying an orientation of the positional marker in the guidance magnetic resonance data. For instance the radiation source may be inserted into the catheter and then the rotational position is determined. The catheter control commands are generated in accordance with the current rotational position. This embodiment may be beneficial because the rotational position of the radiation source is identified by a measurement which reduces the chance that the rotational position determined in air. This makes the procedure safer and leads to a more accurate brachytherapy treatment.

In another embodiment the medical apparatus further comprises a catheter location verification system configured for measuring a catheter position for each of the multiple brachytherapy catheters. Execution of the instructions further causes the processor to measure the catheter position for each of the multiple brachytherapy catheters after receiving the catheter inserted signal for all of the multiple brachytherapy catheters using the location verification system. The location verification system is a system which is used to measure the position or relative position of the catheters to each other. This may be useful for determining if the catheters have moved during the course of treatment. For instance for brachytherapy the patient may have the catheters inserted and then be treated in several different time periods. The use of the catheter location verification system may be useful because it may eliminate the need to make further images to determine the catheter location.

Execution of the instructions further cause the processor to measure a repeat catheter position for each of the multiple brachytherapy catheters after receiving the catheter inserted signal for all the multiple brachytherapy catheters using the location verification system. Essentially after all the catheters have been inserted the location verification system is used to take a measurement which is then used to verify the catheter positions later. Execution of the instructions further cause the processor to generate a catheter position verified signal if the repeat catheter position of each of the multiple brachytherapy catheters is within a predetermined distance from the catheter position. If the catheters are still within a certain distance of each other or a certain absolute location then it is not necessary to re-plan or re-image the catheters.

Execution of the instructions further causes the processor to generate a catheter move signal if the repeat catheter position of each of the multiple brachytherapy catheters is not within a predetermined distance from the catheter position. This embodiment is particularly beneficial because if the repeat catheter position is within the predetermined distance of each other then it may not be necessary to check the position of the catheters before performing therapy after a break. For instance a subject may have the catheters placed and then a physician may perform therapy on the subject. The subject may then have another therapy session hours or even days later. The catheters may be left in place between the different therapy sessions. If the catheters are within the predetermined distance then it may not be necessary to check their position. This would speed the process of performing the therapy and also reduce the need to use expensive imaging equipment such as a magnetic resonance imaging system to confirm the location of the catheters.

In another embodiment execution of the instructions further causes the processor to re-acquire the planning magnetic resonance data using the magnetic resonance imaging system if the catheter move signal is generated. Execution of the instructions further causes the processor to recalculate the catheter control command for each of the multiple brachytherapy catheters using the brachytherapy treatment plan and the re-acquired planning magnetic resonance data. In this embodiment the processor is able to re-acquire the planning magnetic resonance data if the catheter move signal is generated. This may be beneficial because in between therapy sessions the catheters may have shifted or changed position sufficiently that the original catheter control commands are no longer valid.

In another embodiment each of the multiple brachytherapy catheters comprises a tip. The tip comprises a piezoelectric transducer for sending and/or receiving ultrasonic pulses. The catheter location verification system is configured for sending an ultrasonic pulse using the piezoelectric transducer of each of the multiple brachytherapy catheters and receiving the ultrasonic pulse with at least one other of the multiple brachytherapy catheters. Essentially an ultrasonic pulse or sound can be generated at the tip of a particular brachytherapy catheter. By measuring the delay at which the pulse is received by the other brachytherapy catheters or the phase difference of the transmitted and received sound a measure of the relative distance between the different brachytherapy catheters can be developed. The predetermined distance can be expressed in the terms of a time or delay or phase difference instead of in terms of an absolute distance. This may be particularly beneficial because the exact types of tissue and the velocity of ultrasound in between the tips may not be known.

Execution of the instructions further causes the processor to generate the ultrasonic pulse using the piezoelectric transducer of each of the multiple brachytherapy catheters. Execution of the instructions further causes the processor to receive the ultrasonic pulse with at least one other of the multiple brachytherapy catheters. Execution of the instructions further causes the processor to determine a delay for the received ultrasonic pulse. Execution of the instructions further causes the processor to store the delay in the memory as the catheter position. The delay may be translated into an estimated distance or the actual delay may be stored as the catheter position. The catheter position, the repeat catheter position and the predetermined distance may also be interpreted as a measurement which is indicative of a distance such as a delay. This embodiment may be advantageous because it provides a means of inexpensively and accurately determining if the catheters have moved. During a typical therapy session four or five or even more catheters may be placed within a subject.

In another embodiment each of the multiple brachytherapy catheters comprises a shape-sensing fiber optic. The catheter location verification system is configured for measuring the catheter position using the shape-sensing fiber optic of each of the multiple brachytherapy catheters. Execution of the instructions further causes the processor to measure the catheter position using the shape-sensing fiber optic of each of the multiple brachytherapy catheters. Note to self: insert data about shape-sensing fiber optics here. This embodiment may be advantageous because the shape-sensing fiber optics are able to determine an absolute location of the fiber optic which is embedded in the brachytherapy catheter.

In another embodiment execution of the instructions further causes the processor to segment the image reconstructed from the guidance magnetic resonance data to identify catheter locations. Execution of the instructions further causes the processor to display the catheter locations on the display.

In another embodiment the medical apparatus further comprises a catheter actuator configured for controlling the position of the multiple brachytherapy catheters as a function of time. Execution of the instructions further causes the processor to control the position of the multiple brachytherapy catheters by controlling the catheter actuator in accordance with the catheter control commands. This embodiment is beneficial because the medical apparatus is capable of automating the positioning and actuation of the radiation sources within the brachytherapy catheters.

In another aspect the invention provides for a method of using a medical apparatus for guiding a catheter. The medical apparatus comprises a magnetic resonance imaging system for acquiring magnetic resonance data from an imaging zone. The medical apparatus further comprises a display for displaying images. The method comprises the step of receiving a brachytherapy treatment plan for treating a subject. The method further comprises the step of acquiring planning magnetic resonance data using the magnetic resonance imaging system. The method further comprises the step of calculating the catheter placement position and a catheter control command for each of the multiple brachytherapy catheters using the brachytherapy treatment plan and the planning magnetic resonance data.

The catheter control command is descriptive of locations and durations for a radioactive sources within the multiple brachytherapy catheters. The locations in the catheter control commands are the locations of the radiation source within the brachytherapy catheter. The radiation sources can be moved into specific locations of the catheter and held there for a particular period of time for performing a therapy. The method further comprises the step of repeatedly acquiring guidance magnetic resonance data. The method further comprises the step of repeatedly reconstructing an image from the guidance magnetic resonance data. The method further comprises the step of repeatedly displaying the image on the display. The method further comprises the step of repeatedly displaying the catheter placement position on the image.

The method further comprises the step of repeatedly receiving a catheter inserted signal from the user interface. The method further comprises the step of repeatedly segmenting the image to determine the catheter placement position after receiving the catheter inserted signal. The method further comprises the step of repeatedly recalculating the catheter placement for each remaining catheter placement position after receiving the catheter inserted signal. The method further comprises the step of repeatedly recalculating the catheter control command for all of the multiple catheters after receiving the catheter inserted signal. The advantages of this embodiment have been previously discussed.

In another embodiment the method further comprises the step of inserting one of the multiple brachytherapy catheters into the subject for each catheter placement position. The method further comprises the step of adjusting the catheter placement of one of the multiple brachytherapy catheters using the catheter placement position on the image. The image is used as a guide for properly adjusting the position of the catheter placement.

In another aspect the invention provides for a computer program product comprising machine executable instructions for execution by a processor controlling a medical apparatus. The medical apparatus comprises a magnetic resonance imaging system for acquiring magnetic resonance data from an imagining zone. The medical apparatus further comprises a display for displaying images. Execution of the instructions causes the processor to receive a brachytherapy treatment plan for treating a subject. Execution of the instructions further causes the processor to acquire planning magnetic resonance data using the magnetic resonance imaging system. Execution of the instructions further causes the processor to calculate a catheter placement position and a catheter control command for each of the multiple brachytherapy catheters using the brachytherapy treatment plan and the planning magnetic resonance data. The catheter control command is descriptive of the locations and dwell times for the locations for at least one of the multiple brachytherapy catheters.

Execution of the instructions causes the processor for each catheter placement position to repeatedly acquire guidance magnetic resonance data, reconstruct an image from the guidance magnetic resonance data, display an image on the display, display the catheter placement position on the image, in a catheter inserted signal from the user interface segment the image to determine the catheter placement position after receiving the catheter inserted signal, recalculate the catheter placement for each remaining catheter placement position after receiving the catheter inserted signal, and recalculate the catheter control command for all the multiple catheters after receiving the catheter inserted signal. The advantages of this embodiment have been previously discussed.

BRIEF DESCRIPTION OF THE DRAWINGS

In the following preferred embodiments of the invention will be described, by way of example only, and with reference to the drawings in which:

FIG. 11 illustrates how the misplaced catheter of FIG. 10 can be compensated for;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
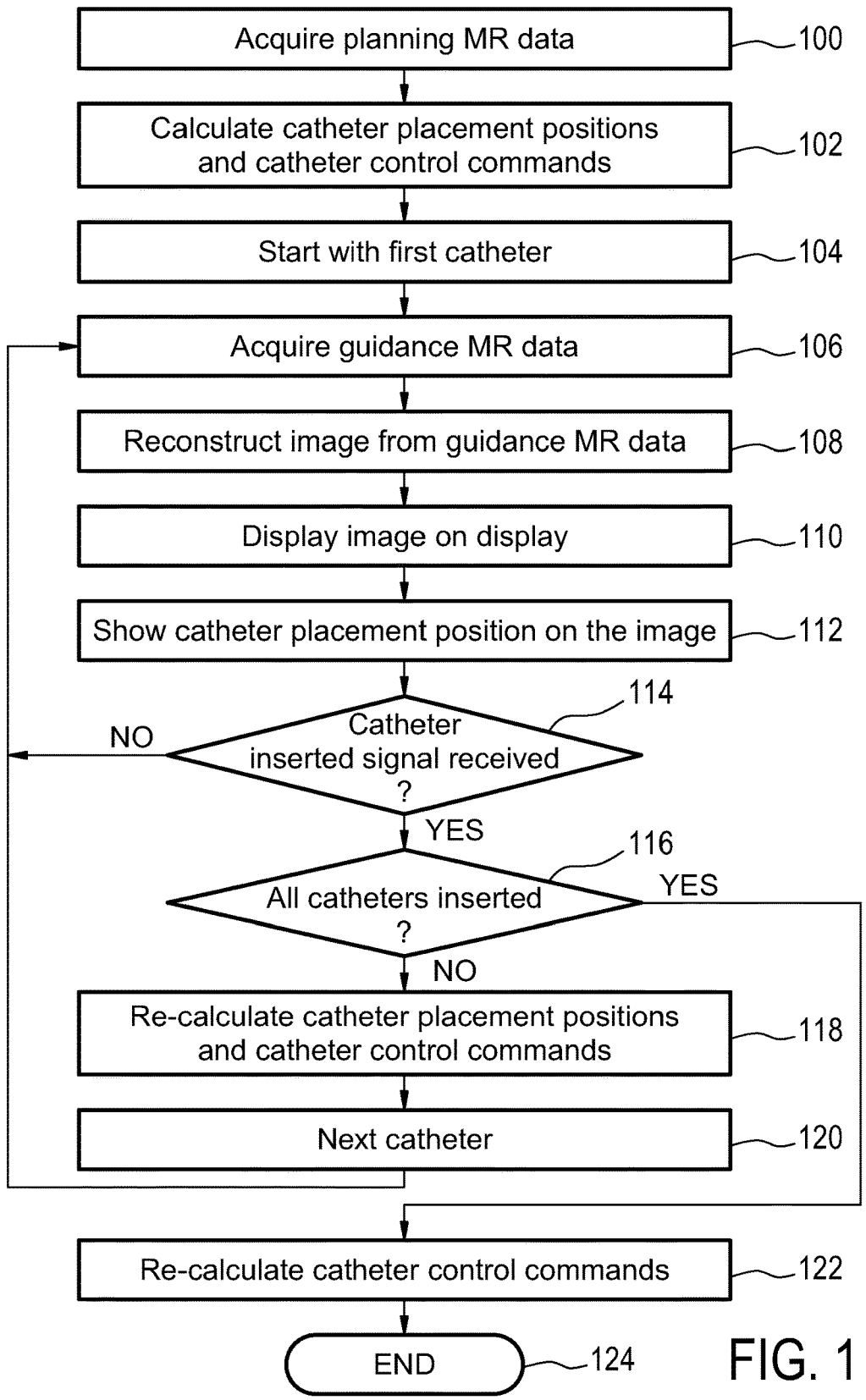
FIG. 1 shows a flow diagram which illustrates a method according to an embodiment of the invention.

FIG. 1 shows a flow diagram which illustrates a method according to an embodiment of the invention. In step 100 planning magnetic resonance data is acquired. Next in step 102 catheter placement positions and catheter control commands are calculated using the planning magnetic resonance data and a brachytherapy treatment plan. The step of receiving a brachytherapy treatment plan is not shown. Next in step 104 the method is performed for the first catheter. In step 106 guidance magnetic resonance data is acquired. An image is reconstructed from the guidance magnetic resonance data in step 108. This image is then displayed 110 on a display. Next in step 112 the catheter placement position that was calculated in step 102 is shown on the image. After one catheter has been inserted a recalculated catheter placement position may be displayed for other catheters. Step 114 is a decision box. The system tests to see if a catheter inserted signal has been received. If the case is no then steps 106-112 are repeated until a catheter inserted signal is received. Essentially the MR data is acquired and then an image is updated to show the location of the catheter relative to the catheter placement position repeatedly.

Once a physician has finished inserting the catheter he is able to signal the system and a catheter inserted signal is received. After the signal is received the method proceeds to step 116. Step 116 is a decision box that asks if all catheters are inserted. If all catheters have not been inserted then the catheter placement positions and catheter control commands are recalculated in step 118. The catheter placement positions for already inserted catheters are not recalculated. The placement positions for catheters which still need to be placed are recalculated. The catheter control commands which essentially describe the position of radioactive source as a function of time are recalculated for all of the catheters. Step 118 may include the step of segmenting one or more magnetic resonance images to determine the location of placed catheters. The method proceeds to the next catheter in step 122. For the next catheter the steps 106-112 are then repeated until a catheter inserted signal is received 114.

If all the catheters have been inserted 116 then the method proceeds to step 122. In step 122 the catheter control commands are recalculated. In some embodiments, the catheter control commands are not recalculated if the catheters are within a predetermined distance or location of the calculated catheter placement positions. Step 122 may include the step of segmenting one or more magnetic resonance images to determine the location of placed catheters. After the catheter control commands have been recalculated, the method ends at step 124.

Figure 2:
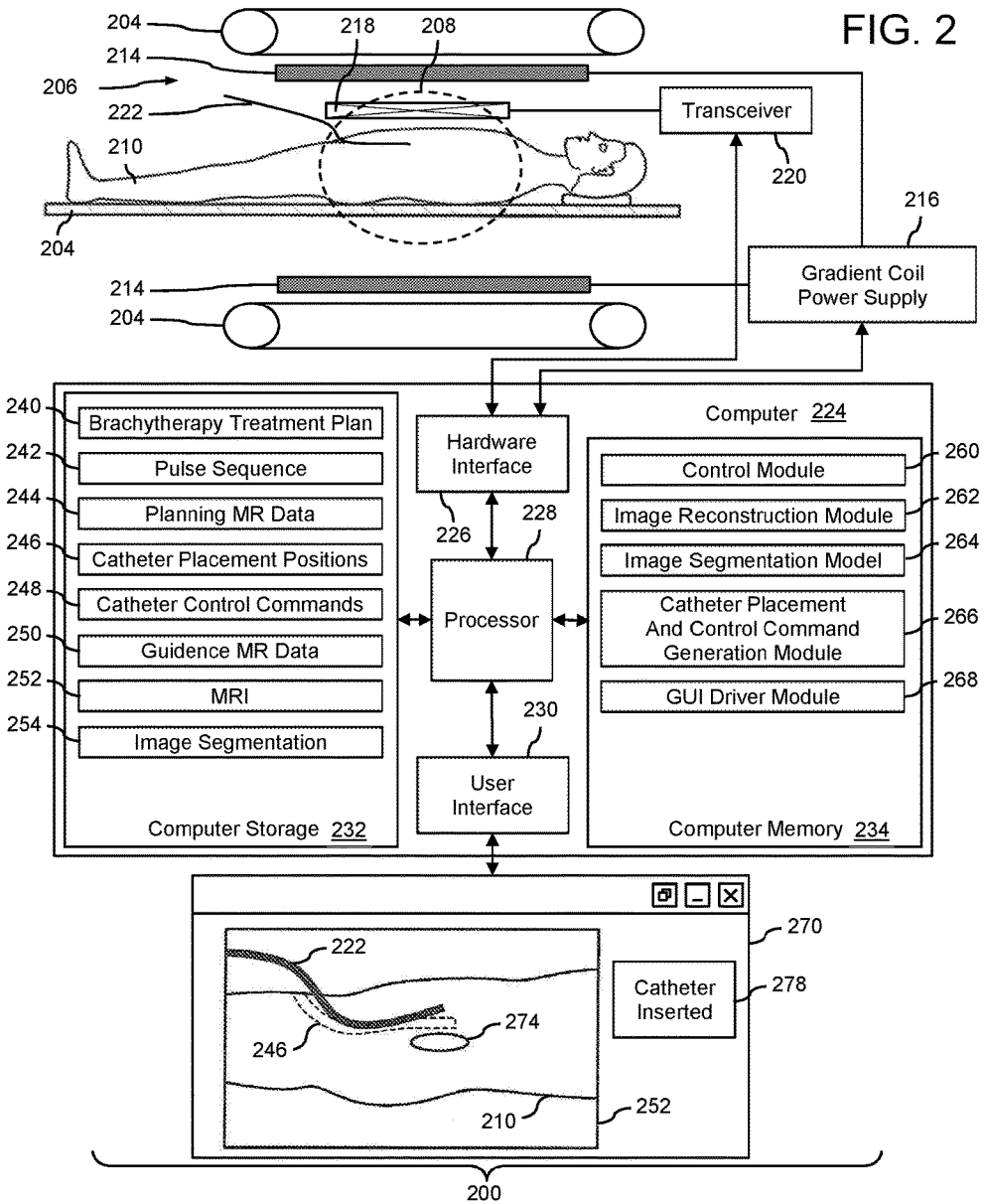
FIG. 2 illustrates a medical apparatus according to an embodiment of the invention.

FIG. 2 illustrates a medical apparatus 200 according to an embodiment of the invention. The medical apparatus 200 comprises a magnetic resonance imaging system 202. In this example the magnetic resonance imaging system 202 comprises a magnet 204. In this example the magnet 204 is a so-called open magnet which uses toroidal magnets above a subject 210. The open magnet has a large open space 206 and an imaging zone 208 in the center. It is advantageous to use an open magnet 204 because it gives more space for a physician to articulate or move a catheter 222. A subject 210 is within the open space 206 and lying partially within the imaging zone 208. The subject 210 is reposing on a subject support 212. Inside the open space 206 there are also gradient coils 214. The gradient coils 214 are connected to a gradient coil power supply 216. Adjacent to the subject 210 and the imaging zone 208 there is a radio-frequency coil 218. The radio-frequency coil 218 is connected to a transceiver 220. A catheter 222 has been inserted into the subject 210. The tip of the catheter 222 is within the imaging zone 208. The transceiver 220 and the gradient coil power supply 216 are connected to a hardware interface 226 of a computer 224. The computer further comprises a processor 228 which uses the hardware interface 226 to control and operate the magnetic resonance imaging system 202. The computer system further comprises a user interface 230, computer storage 232, and computer memory 234 all of which are connected to and controlled by the processor 228.

The computer storage 232 is shown as containing a brachytherapy treatment plan 240. The brachytherapy treatment plan 240 comprises information descriptive of a plan for treating a treatment zone 274 within the subject 210. The brachytherapy treatment plan 240 may also comprise data which is descriptive of paths that a catheter 222 could take towards the treatment zone 274. The computer storage 232 is further shown as containing a pulse sequence 242. The pulse sequence 242 comprises instructions which enable the magnetic resonance imaging system 202 to acquire magnetic resonance data. The computer storage 232 is shown as further comprising or containing planning magnetic resonance data 244. The computer storage 232 is further shown as containing catheter placement positions 246.

The computer storage 232 is further shown as containing catheter control commands 248. The catheter control commands 248 contain detailed instructions on the location and dwell times of radiation sources within the catheters in order to selectively treat a treatment zone 274. The computer storage 232 is further shown as containing guidance magnetic resonance data 250. The computer storage 232 is further shown as containing a magnetic resonance image 252 constructed from the guidance magnetic resonance data 250. The computer storage 232 is further shown as containing an image segmentation 254. The image segmentation may represent an image segmentation locating placed catheters and/or it may also represent an image segmentation 254 which identifies key elements of the subject's 210 anatomy which enable the calculation of the catheter placement positions 246. This may for instance include orifices and/or pathways through veins and arteries.

The computer memory 234 is shown as containing a control module 260. The control module comprises computer executable code which enables the processor 228 to control the operation function of the medical apparatus 200. The control module 260 may use the pulse sequence 242 to acquire the planning magnetic resonance data 244 and/or the guidance magnetic resonance data 250. The computer memory 234 is shown as further containing an image reconstruction module 262. The image reconstruction module 262 may be used for reconstructing magnetic resonance images from the planning magnetic resonance data 244 and/or the guidance magnetic resonance data 250. For instance the image reconstruction module 262 may be used to reconstruct the magnetic resonance image 252 from the guidance magnetic resonance data 250.

The computer memory 234 is further shown as containing an image segmentation module 264. The image segmentation module may be used for segmenting magnetic resonance images 252 for identifying key anatomical locations within the subject 210 and also for identifying the locations of catheters 222 that have been placed. The image segmentation module 264 may also be used for identifying fiduciary markers located on the subject 210 and/or the catheters 222. For instance a catheter may have a fiduciary mark which enables the identification of the location and orientation of the catheter. In some embodiments a radioactive source may also have a fiduciary mark which may be identified by the image segmentation module 264. The computer memory 234 is further shown as containing a catheter placement and control command generation module 266. The catheter placement and control command generation module 266 contains computer executable code which may use the brachytherapy treatment plan 240, the planning magnetic resonance data 244, the guidance magnetic resonance data 250, and/or the magnetic resonance image 252 to generate the catheter placement positions 246 and/or the catheter control commands 248.

The computer memory 234 is further shown as containing a graphical user interface driver module 268. The graphical user interface driver module 268 is configured for driving a graphical user interface 270. The graphical user interface 270 is shown as being operated by the user interface 230. For instance the graphical user interface 270 may be displayed on a computer monitor, display or tablet computer. The graphical user interface 270 displays a magnetic resonance image 252. Within the magnetic resonance image 252 a subject 210 with a catheter inserted 222 is shown. A catheter placement position 246 is superimposed on the subject 210. A treatment zone 274 is also superimposed on the image of the subject 210.

When inserting the catheter 222 a physician or other healthcare provider may use the displayed catheter placement position 246 as a guide to where to place the catheter 222. It should be noted in this image that the catheter 222 is not placed exactly where the catheter placement position 246 is located. Once the physician or healthcare provider has placed the catheter 222 he or she may click the catheter inserted button 278. This sends a catheter inserted signal from the user interface 230 to the processor 228. The processor 228 may then segment the image 252 and identify the location of the catheter 222. The processor 228 may then if the catheter is outside of a predetermined distance from the catheter placement position 246 recalculate the remaining catheter placement positions 246 and recalculate all of the catheter control commands 248.

Figure 3:
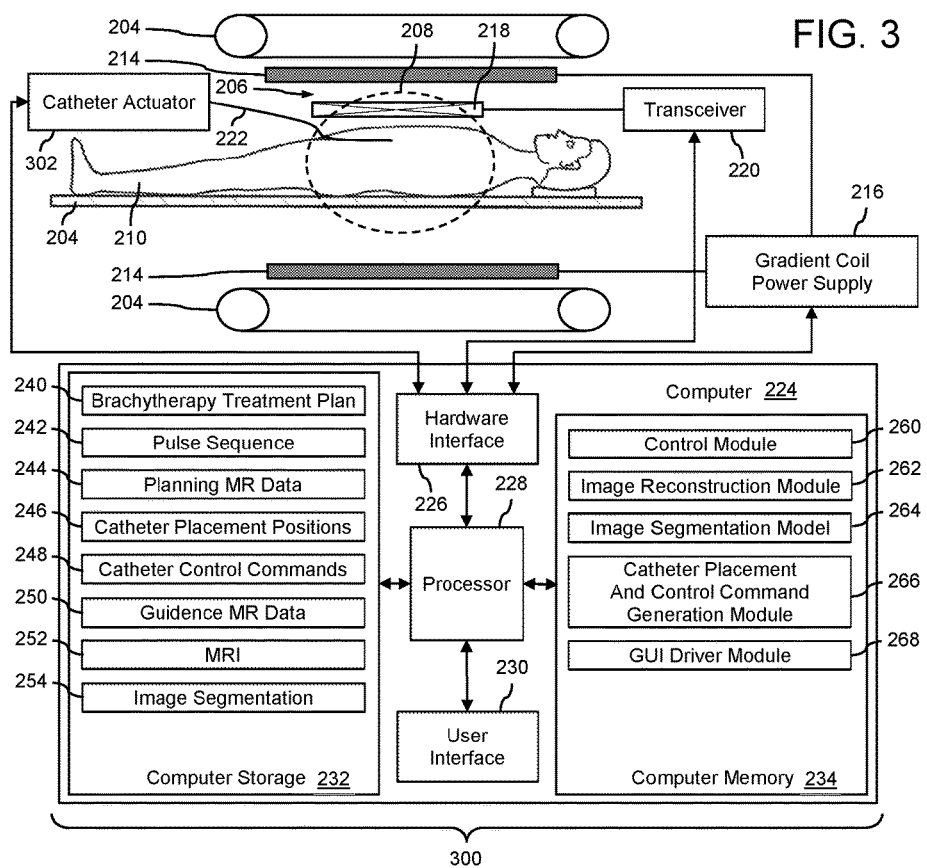
FIG. 3 illustrates a medical apparatus according to a further embodiment of the invention.

FIG. 3 shows an embodiment of a medical apparatus 300 according to an embodiment of the invention. The embodiment shown in FIG. 3 is similar to that shown in FIG. 2. In this embodiment there is a catheter actuator 302 attached to the catheter 222. The catheter 222 is intended to possibly represent multiple catheters inserted in the subject 210. The catheter actuator 302 is configured for controlling the position of a radioactive brachytherapy source within each of the catheters 222 as a function of time. In this embodiment the processor 228 executes the control module 260. The control module 260 uses the catheter control commands 248 to control the catheter actuator 302. In this way the medical apparatus 300 can perform an automated radiotherapy of the subject 210. In an alternative embodiment the medical apparatus only comprises the catheter actuator 302. In yet another embodiment the magnetic resonance imaging system 202 and the catheter actuator 302 are located at separate positions. For instance the catheters may be inserted while the subject 210 is within the magnetic resonance imaging system 202. The subject 210 may then be moved to a separate location where the radioactive sources are inserted into the catheters 222 and then are connected to the catheter actuator for actuation.

Figure 4:
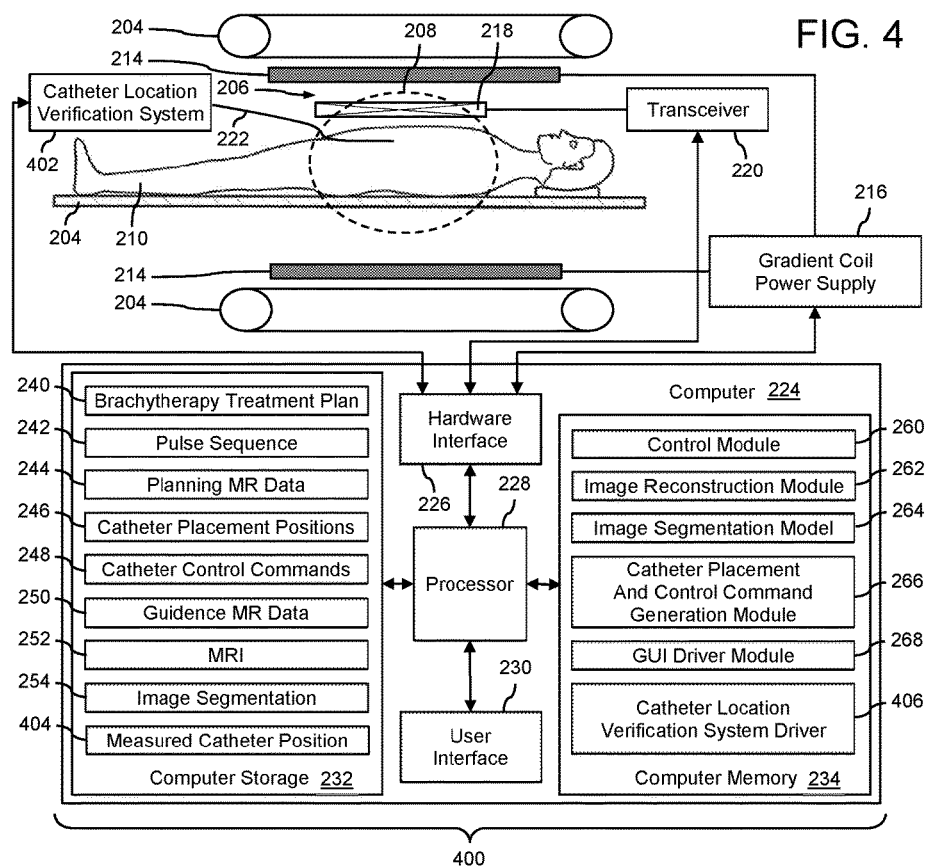
FIG. 4 illustrates a medical apparatus according to a further embodiment of the invention.

FIG. 4 shows a medical apparatus 400 according to a further embodiment of the invention. The medical apparatus 400 is similar to that shown in FIGS. 2 and 3. The embodiment shown in FIG. 4 shows a catheter location verification system 402. The catheter location verification system 402 is connected to two or more catheters 222. The catheter location verification system 402 is connected to the hardware interface 226. The catheter location verification system 402 uses a sensor or sensors to determine the absolute or relative position of catheters 222 with respect to each other. This may be useful in determining if the catheters 222 have moved in between treatment sessions. For instance shape-sensing fiber optics and/or piezoelectric transducers at the tips of the catheters 222 may be used. The computer storage 232 is shown as containing a measured catheter position 404. These may be absolute locations or they may be sensor readings taken from the catheters 222 by the catheter location verification system 402.

The computer memory is further shown as containing a catheter location verification system driver 406. The catheter location verification system driver 406 contains computer executable code which enables the processor 228 to control the catheter location verification system 402 and acquire the measured catheter position 404. The feature shown in FIGS. 3 and 4 may be combined. In some embodiments the magnetic resonance imaging system 202 is not present. That is to say the catheter location verification system 402 may stand alone. This may be useful in some situations for instance a catheter location verification system 402 may be used to take the measured catheter position 404 immediately after the catheters 222 are inserted into the subject 210 while the subject 210 is still within the magnetic resonance imaging system 202 and has not been moved. The subject 210 may then be moved to a different location for performing a brachytherapy treatment session. Before the brachytherapy is performed the subject 210 may be connected to a different catheter location verification system 402 or the same one moved to the same location. This may be used to verify the catheter locations before the beginning of a therapy.

Figure 5:
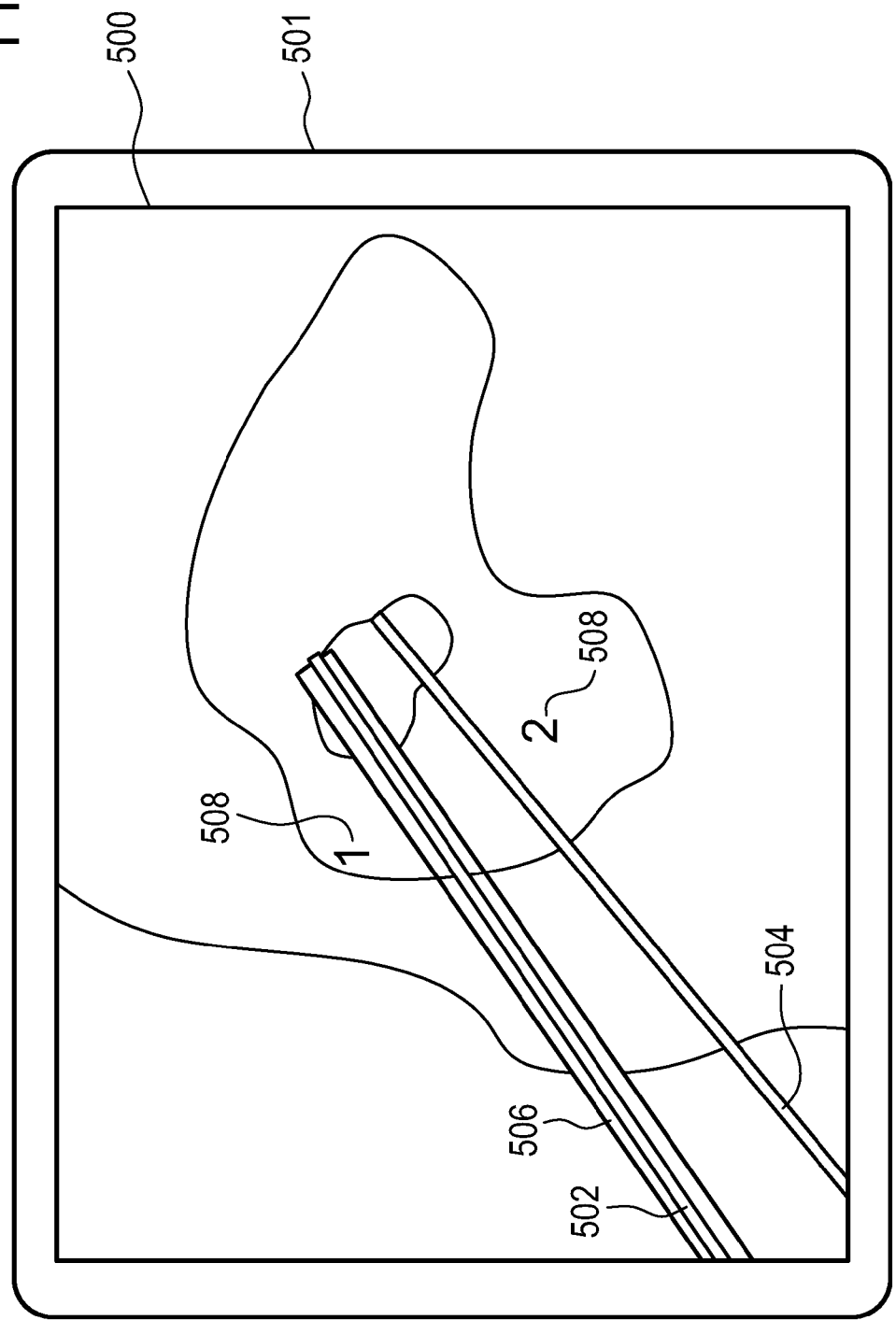
FIG. 5 shows a drawing of a magnetic resonance image.

FIG. 5 shows a drawing of a magnetic resonance image 500 that could be displayed in a graphical user interface 501 of a medical apparatus according to an embodiment of the invention. Superimposed on this magnetic resonance image 500 is a first catheter placement position 502 and a second catheter placement position 504. The physician or healthcare provider may use these two positions 502, 504 as a guide for inserting a catheter 506. There is a catheter 506 being inserted along the first catheter placement position 502. After this catheter 506 is inserted the physician or healthcare provider may insert a second catheter along the second catheter placement position 504. FIG. 5 illustrates a possible way to display catheter information on top of real time images during an intervention. In this example the intervention list may insert catheter 506 along first catheter placement position 502. The second catheter placement position 504 is displayed on the image 500 although the second catheter has not yet been inserted. Apart from the display of catheter placement positions 502, 504 the graphical user interface could also show some additional information like identification numbers 508 to identify the different catheters.

Embodiments of the invention may provide for a procedure for optimized placement of catheters used for high dose rate brachytherapy using magnetic resonance imaging guidance. This may include the use of a computer algorithm to find the optimal catheter arrangement, a method to assist the interventionalist in inserting the catheters at the optimum positions, and a method to verify the positioning at a later time.

In particular, embodiments may provide for conventional treatment planning algorithms with a simplified algorithm, using only a limited number of reference points for dose calculations. Such a calculation is sufficiently fast and flexible to find a good initial guess for catheter positions and to quickly determine small corrections during the intervention. In combination with a real-time MR-guided interventional technique, the placement of brachytherapy catheters can be improved significantly compared to conventional procedures.

In some embodiments verification of catheter positions may be independent of medical imaging modalities. In this way it is possible to verify the catheter position directly before the start of the treatment session without the need of moving the patient.

In brachytherapy, placement of the radioactive seeds is extremely critical. Since the radiation dose which can be delivered to the tumor region is limited by the maximum dose compatible with organs at risk close to the tumor, an optimum distribution of dwell times and positions of the radiation sources with respect to both tumor volume and surrounding organs must be found.

If the catheters, through which the radioactive sources are inserted, are not placed at optimum positions, the required restriction of the dose rate to safe conditions will consequently lead to a less effective tumor treatment or to a larger number of applicators to be placed to achieve the same treatment efficiency associated with a higher level of invasiveness of the procedure. The following issues (numbered 1 through 4) may be addressed by embodiments of the invention:

1. In conventional HDR brachytherapy, optimization of the source positions and dwell times is done by a software tool after the interventional process, i.e. when the catheters are already in place. However, the catheter positions themselves do not necessarily represent the optimum arrangement, since they are suggested by the physician and not optimized by an algorithm. Embodiments may overcome this problem by suggesting optimized spatial arrangements of the catheters to the radiologist or radiation oncologist.

2. Additionally, the physician may have to place a large number of catheters to achieve the desired dose distribution. Embodiments of the invention may automatically optimize the arrangement in such a way that the number of catheters required is minimized. This can help to avoid unnecessary interventions.

3. The actual placement of the catheters performed by the interventionalist, even if carried out under image guidance, can never be perfectly exact either. The final treatment plan calculated after the intervention can then only be optimized according to the then fixed catheter positions. To overcome this disadvantage, embodiments of the invention may offer on-line corrections of the catheter placement plan shown to the interventionalist during the intervention procedure. After having placed one catheter, the ideal arrangement of the following catheters is updated taking the position of the already inserted catheter into account.

It is important to note that neither the pre-interventional planning nor the online corrections can replace the final treatment plan to be calculated after the intervention. Only the final planning, approved by a radiation oncologist, may be used for the actual treatment. The only purpose of the dose calculations performed before and during the intervention is to assist the interventionalist in placing the catheters at optimum positions.

4. HDR brachytherapy is often split into several sessions. This so-called fractionation allows healthy tissue to recover, while tumor cells are generally less efficient in repair between fractions. It also allows tumor cells to cycle into a radio-sensitive phase of the cell cycle before the next fraction is given. Fractionation therefore further improves the effect of the therapy. The catheters often remain in the patient's body during the course of the whole therapy. If the position of the catheters changes slightly between the sessions, the original treatment plan may have to be corrected. It is usually not feasible to take MR images of the catheters at the beginning of each session. Apart from the additional cost, time and effort related to MR imaging, the treatment takes place within a radiation-shielded area of the radiology department, where MR scanners are usually not available. Even if images were taken directly before the session, the patient would still have to be moved before the start of the treatment, so that the measured catheter positions may not be reliable.

The invention proposes a scheme for quick and easy verification of the catheter positions before the start of the treatment session without the need for medical imaging modalities, while the patient can remain in the same position for catheter verification and treatment.

Some embodiments of the invention may have the following features or elements:

1. A system for MRI-guided focal therapy with on-line therapy planning updates including:
2. An MRI system with appropriate extensions allowing real-time monitoring of interventional procedures
3. An extended planning system to define the optimum catheter positions before the intervention
4. An application visualizing the pre-defined catheter paths during the intervention, so that the interventionalist can follow the paths precisely
5. A dedicated MR imaging sequence to determine the catheter positions in relation to the original planning image
6. A communication device (e.g. button, pedal) to allow the interventionalist to inform the software when one catheter is in place and the system should proceed with the next one
7. An online optimization algorithm to adapt the suggested further catheter positions to slight misalignments each time a catheter has been inserted
8. Methods to verify the catheter positions in the MRI environment immediately after the placement of the catheters & before each treatment session, in particular employing catheters equipped with e.g. piezoelectric transducers for mutual distance measurement. These methods also require readout electronics to be connected to the catheters for performing a measurement.

Embodiment of the invention may provide for extensions of the MRI system that include in-room displays, controls and a application-specific software solution incl. data linkage to the therapy planning module and image databases.

Embodiment of the invention may provide for optimized treatment planning before the intervention.

An existing treatment planning algorithm (e.g. inverse planning by simulated annealing) is extended to a broader parameter range, in order to optimize not only the dwell properties within the catheters, but also the positions of the catheters themselves. This can be realized in the following way:

First, a reasonable catheter arrangement is determined using a fast algorithm: For this purpose, dose calculation can be restricted to a limited number of reference points on critical surfaces (the approach is similar to the online optimization during the intervention described below). This restriction makes very fast optimization of seed dwell parameters and iteration of catheter positions possible. The algorithm varies the positions and angulation of the catheters subject to constraints approved by the physician in terms of anatomically feasible needle pathways. Furthermore, the algorithm tries to minimize the total number of required catheters.

Second, a conventional planning algorithm calculates the exact dose distribution with the catheter arrangement obtained in the first optimization step. Fine-tuning of the catheter positions is now possible by calculating optimum treatment plans for a number of slightly varied catheter arrangements. By iterating such a calculation, catheter positions can be found which yield the best possible treatment plan. Since a good "initial guess" for the catheter arrangement had already been determined in the first step, only a small number of iterations for this time-consuming calculation will be necessary.

Embodiment of the invention may provide for an interventional magnetic resonance system envisaged for the described procedures already includes a display showing real-time MR images to the interventionalist. This display must be extended to visualize the following information:

the ideal position and orientation of the catheters as calculated as well as the position of the catheter which is currently being inserted the delineated target and organs at risk optionally the (optimum) dose distribution in space to be expected with the current arrangement of catheters and/or the planned dose distribution Embodiment of the invention may have the feature that catheter positions are calculated with respect to a planning image acquired before the intervention. In order to view the proposed needle path on the real-time images, coordinates of the planning image must be mapped to the real-time images. If the organs under consideration do not move significantly during the intervention, the system can use a fixed coordinate frame which is defined once before the interventions by specifying one or more points in space and relating them to points in the planning images. If motion of the organs cannot be excluded (e.g. respiratory motion), there are several options:

a. The motion is detected from the real-time images, those with accurate geometrical correspondence to the planning data are highlighted or visually stressed by some appropriate means. The simplest implementation uses a coronal and a transverse real-time imaging slice but with geometries planned according to the pre-operative data and the planning result. Both real-time slices are meant to always contain the needle during advancement. The paracoronal plane will additionally always show the lesion as it moves with the respiratory cycle while the paratransverse plane will only show the lesion if motion state of the planning data and real-time data match.

b. The respiratory cycle is detected and images are obtained using a gating technique. This method has the disadvantage of being slow and in some cases inaccurate.

c. Planning images and real-time images are compared automatically; distortions and displacements are determined by a computer algorithm. This may require the acquisition of multiple images.

Embodiment of the invention may provide for magnetic resonance imaging sequences that are used to optimally support the workflow including planning, real-time guidance, and verification of the procedure or parts of it.

For procedure planning visualization of the organ, the target lesions and structures and organs at risk are important. Depending on the type of tumor and organ, a set of scans will be required: DCE for imaging of the organ and the tumor(s), T1W-3D-TFE for overall display of anatomy including surrounding organs. Diffusion- and T2W-weighted imaging for further specification of the tumors, are just very likely examples. Also Diffusion and T2 quantification may become relevant future methods.

For real-time guidance, imaging will be typically performed in one or several interleaved 2D imaging stacks. Using several interleaved imaging stacks is advantageous for tumors in moving organs such as liver or deformable organs as breast. In the specific case of liver, typically, a coronal view will be used to continuously monitor the position of the lesion during respiration. The paracoronal view will be chosen such to additionally contain the planned needle axis while a paratransverse view can be added to immediately detect out-of-plane needle advancement in both imaging planes.

The multi-stack approach has advantages in cases where ultimate accuracy is required, such as for small lesions (e.g. mamma). The geometries of the stacks can be derived immediately from the earlier planning iteration result. It is possible to optimize the individual stacks for their intended purpose, e.g. it is possible to choose field of view, frame rate and resolution individually (e.g. for the liver example, to resolve the respiratory motion induced motion of the target lesion optimally, the frame rate of this stack (=stack 1) can be increase in relation to the transverse stack (=stack 2)) by simply using as sequence like 1, 1, . . . , 2. Fold-over and read-out can be chosen optimally so the needle artifact is favorable: e.g. it could be desirable to have a thick needle artifact in the images of stack 1 for robust guidance while it would be desirable to have a thin accurate artifact in the images of stack 2, so both stacks together would deliver robust tracking and accurate position measurements at the same time.

Generally, multiple imaging stack sequences benefit from appropriate display of the data: In a simple case two orthogonal stacks planned to contain the needle can be displayed in 3D to additionally immediately visualize the section line and thus the planned needle path in 3D as well. Stacks can also be measured at the same geometry but, as mentioned, with different content or, technically more advanced, even different types of contrast and sequences (T1W, T2W, T1/T2W, IR, 2D, 3D). Such techniques will be valuable for applications requiring more sophisticated methods for tumor characterization (e.g. prostate). For such data overlay techniques may apply to optimally represent the data.

Verification scans will typically be performed to confirm and assess intermediate and final results of the procedure. One example is to measure the proper placement of devices such as needles, catheters or guide-wires. Such scans could be automatically planned and performed such that an optimal assessment is possible, e.g. by preparing a set of images to optimally visualize the tip of the device in a given respiratory state while immediately afterwards performing a set of images, (partly) guided by the prior information, to visualize the target lesion or adjacent organs/structures (at risk) in the same respiratory state with high relative accuracy to the previous scan.

The information from the verifications scans or from additionally, subsequently acquired images are immediately ideally suited to be fed into the on-line therapy planning module (device positions, target lesion update (swelling may have occurred), update organs at risk (again swelling may have occurred). Together with such verification scans, targeted complication detection scans can be included using above-measured parameters. E.g. if a certain probability for bleeding in a neighbor organ or near a critical vessel along the needle path is deduced, a respective scan could be recommended or automatically performed.

Embodiment of the invention may provide for a method where once a needle is in place, the interventionalist is able to instruct the computer to perform an online optimization, to visualize the next needle path to be followed and to make according adjustments for the subsequent MRI scans.

This can be realized by an additional input function of the interventional software suite using a foot pedal, a mouse, a touchpad, a button, a camera tracking system or any other means suitable in a clinical environment.

Despite the use of advanced image-guidance during the insertion, a catheter can be misaligned. In this case, Embodiment of the invention may provide for a method of slight position correction of the remaining catheters may be necessary to ensure the best possible dose distribution.

In order to suggest these corrections, the computer first needs to determine the actual catheter position. This can be realized by analyzing the acquired real-time images or by using markers on the catheters. It is then in principle possible to use the same optimization procedure as in the initial planning before the intervention, keeping the already placed catheters fixed. Even with today's computer hardware, such an optimization procedure may very well take several minutes or more, which increases the time needed for the whole intervention significantly.

Since only a slight deviation from the initial plan is to be corrected, a much faster calculation method is proposed in the following.

Multiple reference points are defined in space, preferably on the surfaces of delineated lesions or organs at risk. Starting with the initially calculated optimum source distribution, the dose is now calculated only at these few points using a simple summation over point or line sources with essentially $1/r^2$ behavior.

This can be expressed by the geometry function $G(r,\theta)$. All constants and higher-order terms can probably be neglected, since only small deviations from the initial state are of interest and absolute values are not necessary. For reference point i and source positions j this simplified dose is $$d_i^{(0)} = \sum_j t_j G(r_j, \theta_j),$$

where $t_j$ is the dwell time at position j. When a needle is in place, only the deviations from these initially calculated values are determined and optimized by varying the source positions and dwell times, thereby minimizing the sum of squares, $$\min\left[\sum_i (d_i^{(0)} - d_i^{(1)})^2\right],$$

where $d_i^{(0)}$ are the doses at the reference points with the new catheter arrangement. The concepts behind this algorithm are illustrated in a simple example illustrated in FIGS. 6 through 8.

Figure 6:
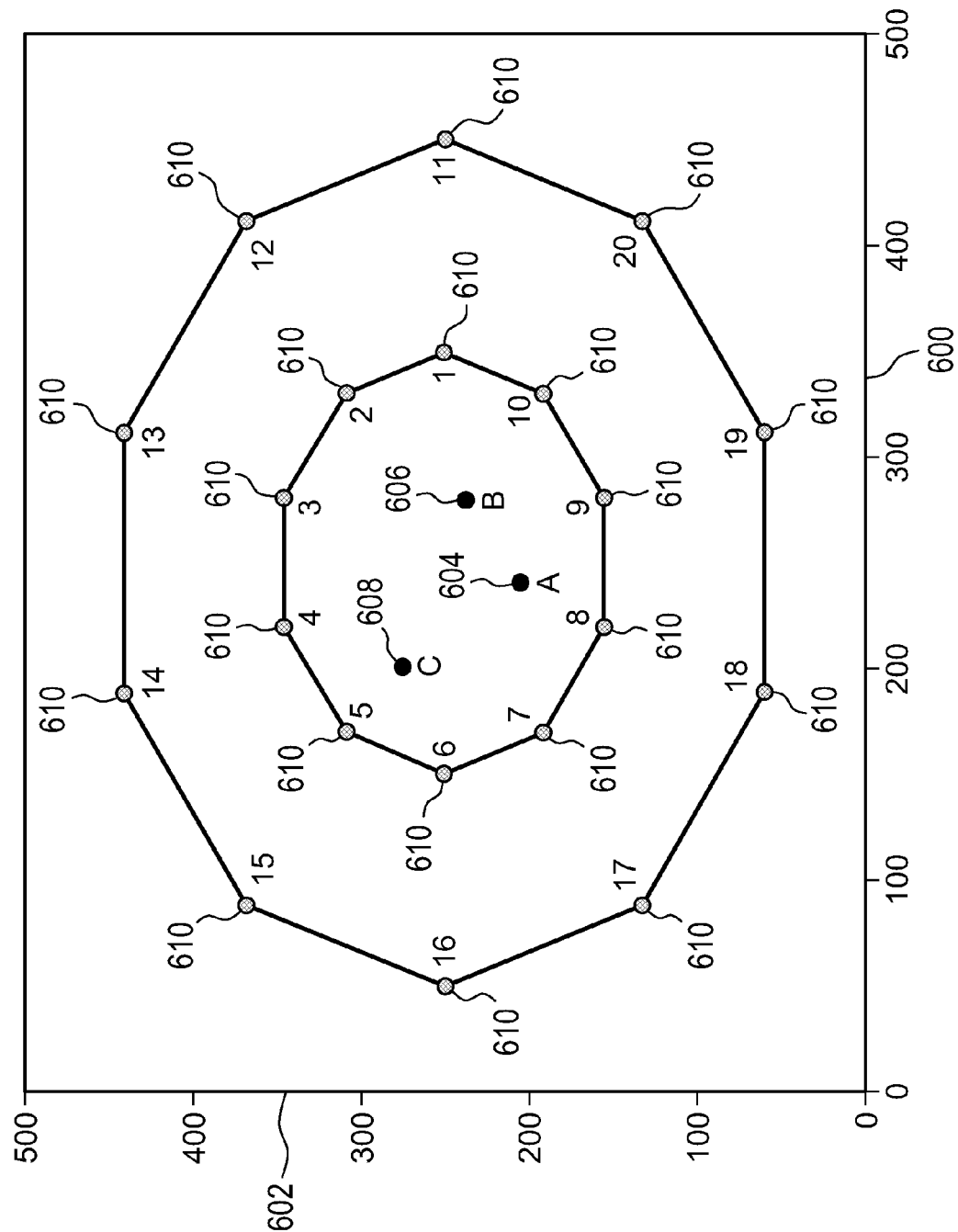
FIG. 6 shows a brachytherapy treatment plan according to an embodiment of the invention.

FIG. 6 shows a brachytherapy treatment plan according to an embodiment of the invention. The x-axis labeled 600 is a first directional dimension in arbitrary units. The y-axis labeled 602 is a second directional dimension in arbitrary units. Within the center there is the location of a first brachytherapy radiation source 604, a second brachytherapy radiation source 606, and a third brachytherapy radiation source 608. Surrounding these locations for the radiation sources 604, 606, 608 are 20 reference points 610. The reference points 610 may for instance be anatomical locations within a subject.

Figure 7:
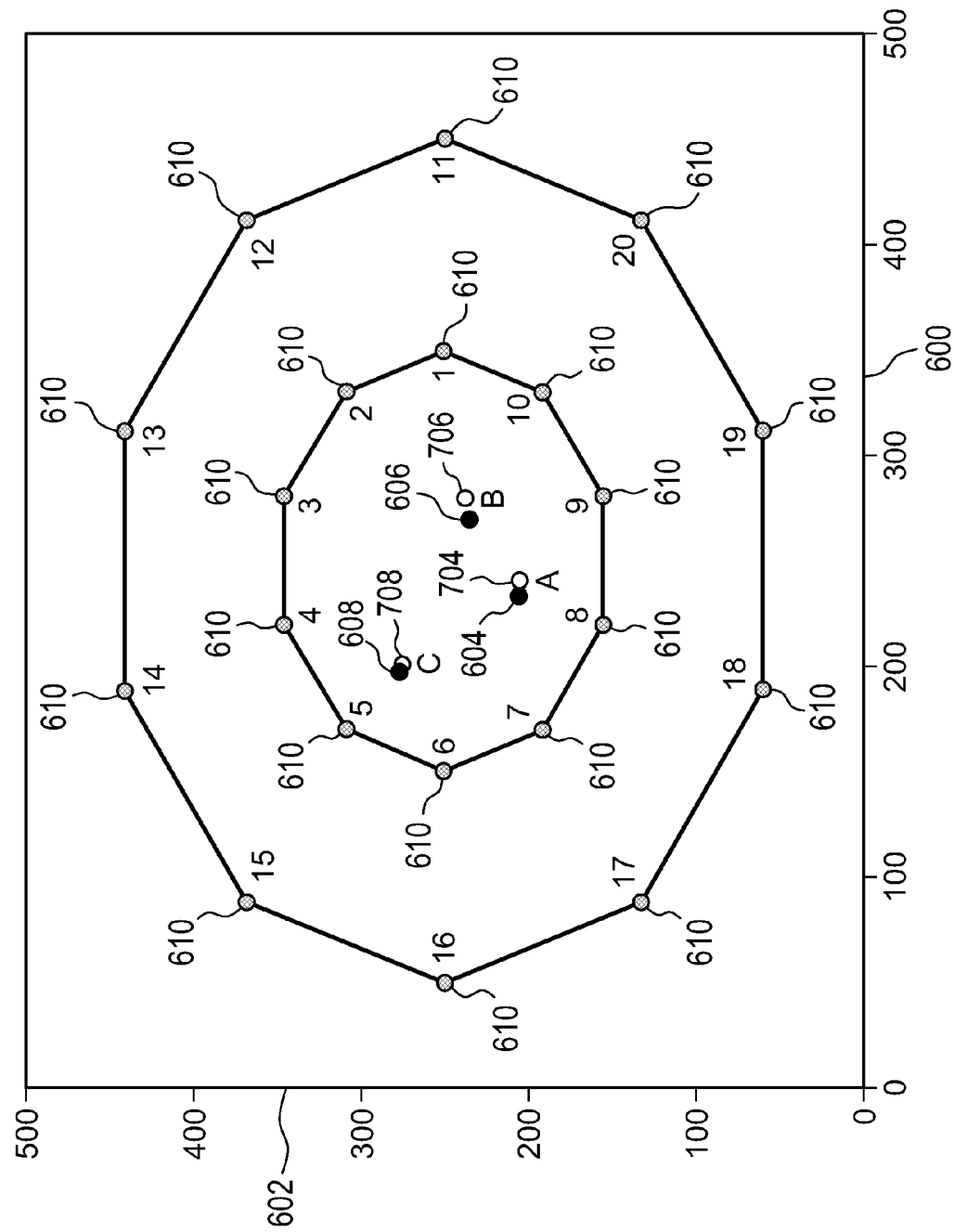
FIG. 7 illustrates how the brachytherapy treatment plan of FIG. 6 can be changed by a misplaced catheter.

FIG. 7 illustrates how the brachytherapy treatment plan can be changed by a misplaced catheter. In FIG. 7 the reference points 610 are identical to that shown in FIG. 6. In this example the original placements of the radiation sources 604, 606 and 608 are shown. However, when the intervention list inserted the catheter the catheter for point 604 was misplaced. The actual placement is shown as position 704. To compensate for this the second brachytherapy radiation source is repositioned at location 706 and the third brachytherapy radiation source is relocated to position 708.

Figure 8:
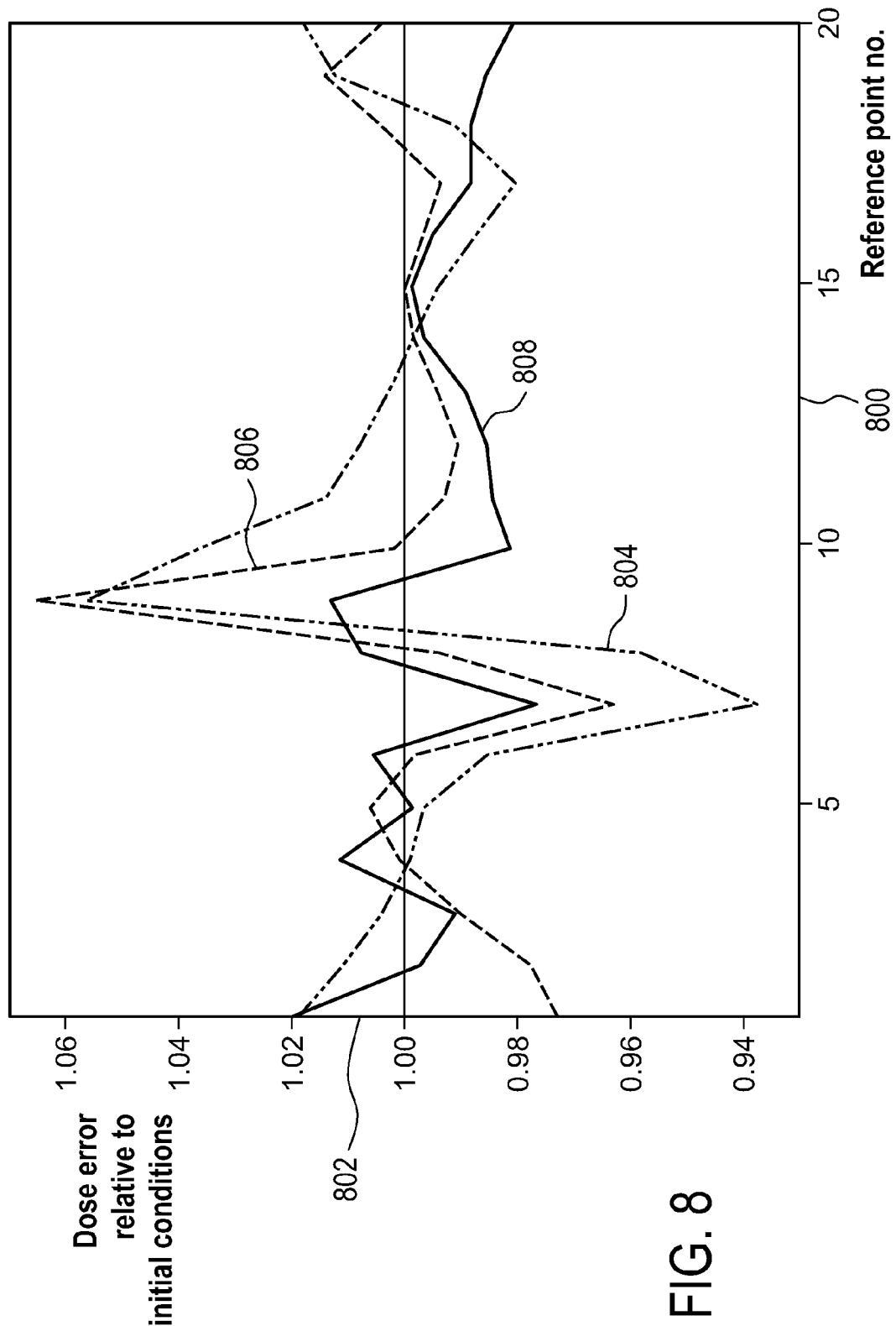
FIG. 8 illustrates the advantage of shifting the locations of the brachytherapy radiation sources in response to the misplaced catheter of FIG. 7.

FIG. 8 illustrates the advantage of shifting the locations of the second 706 and third 708 brachytherapy radiation sources in response to the misplacement of the first brachytherapy radiation source 704. The x-axis labeled 800 shows the dose air 802 for each of the reference points 800. The curve labeled 804 shows the deviations of the dose deposited at the reference point after the misplacement of a relative to the initial planning without any correction. The curve labeled 806 shows only correction of the optimized dwell times. That is to say the locations 606 and 608 are used. The curve labeled 808 shows the effect of correcting both the dwell times and using the corrected positions 706 and 708.

In FIGS. 6 through 8 we start with an initial distribution of dwell positions A, B, and C, the dose distribution in a number of reference points is calculated according to a very simple scheme—in this case, it is just the sum of point sources with $1/r^2$ behavior. After placing the first needle with a slight misalignment, dwell position A is shifted to the right. The algorithm then calculates corrections for the remaining dwell positions and the dwell times to keep the deviations of the dose in the reference points (compared to the initial conditions) as small as possible.

As can be seen from FIG. 8, this procedure significantly reduces the errors due to the first needle misalignment (red curve compared to blue curve). Without spatial realignment, optimization of the dwell times only does not yield such a good result (green curve).

This implementation of an optimization algorithm can easily be extended to allow for weighting of the reference points or for restrictions on the possible motion of the dwell positions (e.g. only along catheter tubes).

Figure 9:
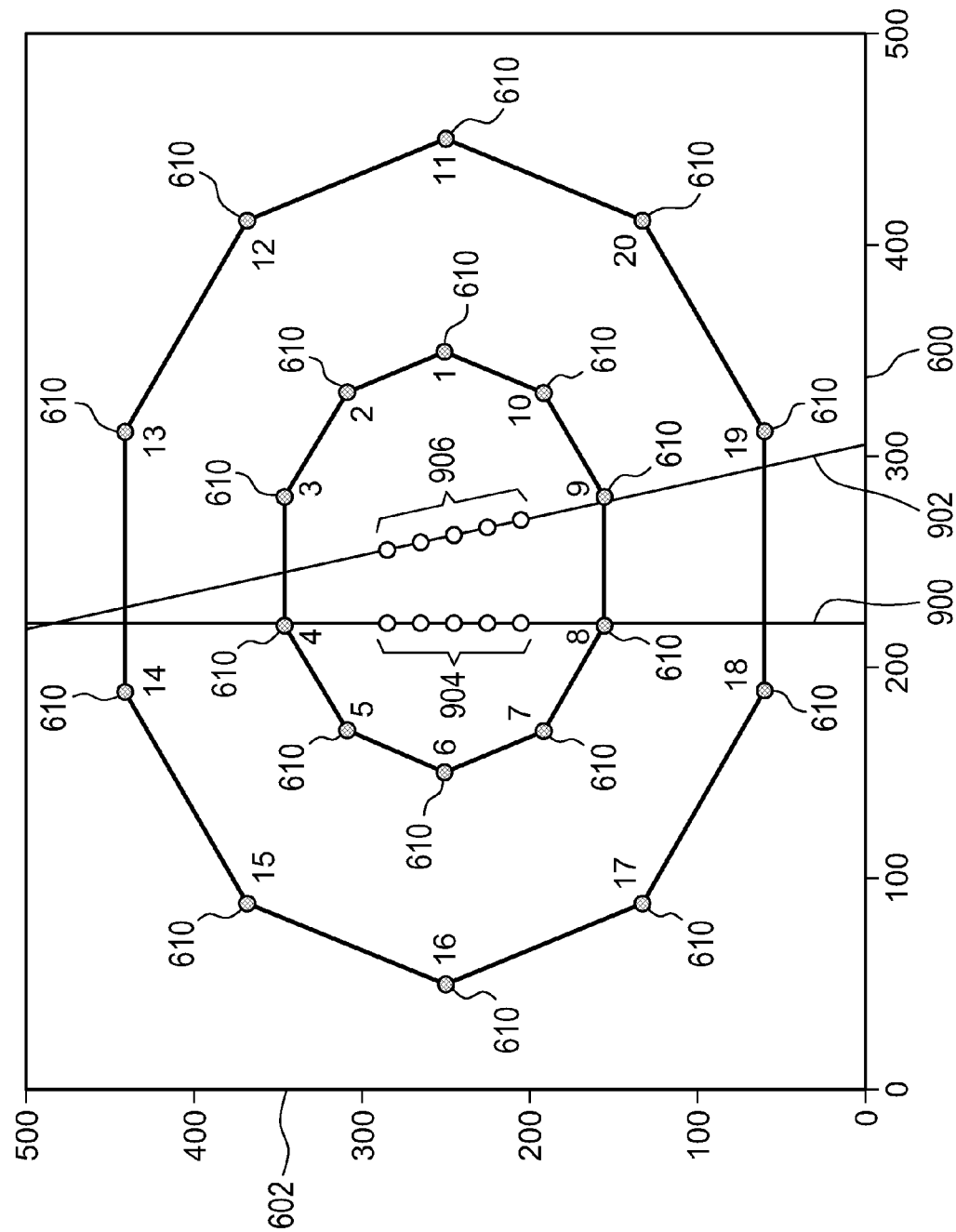
FIG. 9 shows a brachytherapy treatment plan according to a further embodiment of the invention.

FIG. 9 shows a different example of a brachytherapy treatment plan. This is similar to that shown in FIG. 6 except a first catheter placement position 900 is shown and a second catheter placement position 902 is shown. Along each of these catheter placement positions 900, 902 are dwell locations for brachytherapy radiation sources. Along the first catheter placement position 900 there are four dwell locations of a first radiation source 904. Along the second catheter placement position 902 there are four dwell locations 906 of a second radiation source 906. The radius of the dwell locations 904, 906 is an indication of the relative length of the dwell time.

Figure 10:
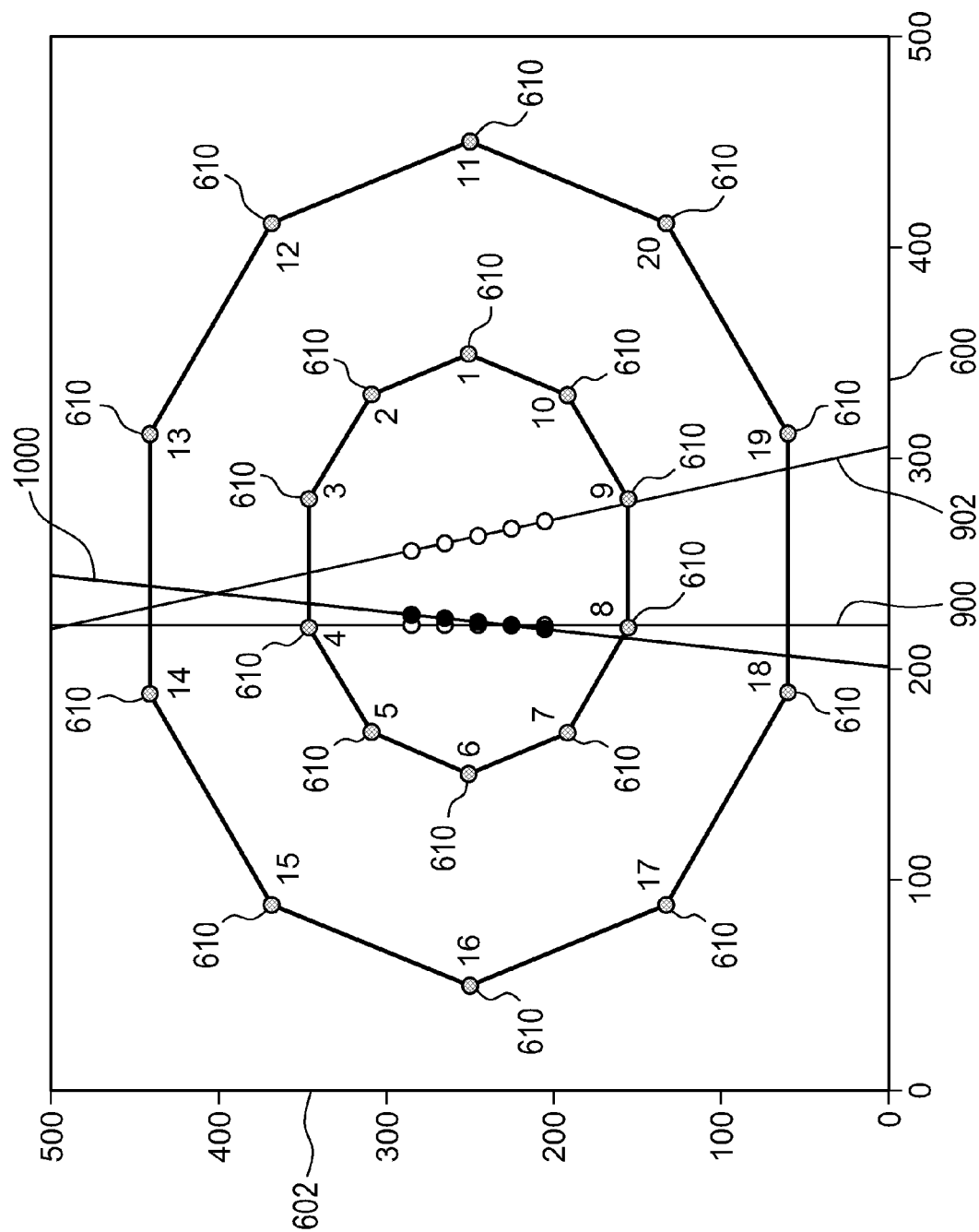
FIG. 10. shows the brachytherapy treatment plan of FIG. 9 with a misplaced catheter.

FIG. 10 is identical to that of FIG. 9 except in FIG. 10 a first catheter has been inserted, but is misaligned. Line labeled 1000 and the five points on this line indicate the five misaligned dwell locations.

Figure 11:
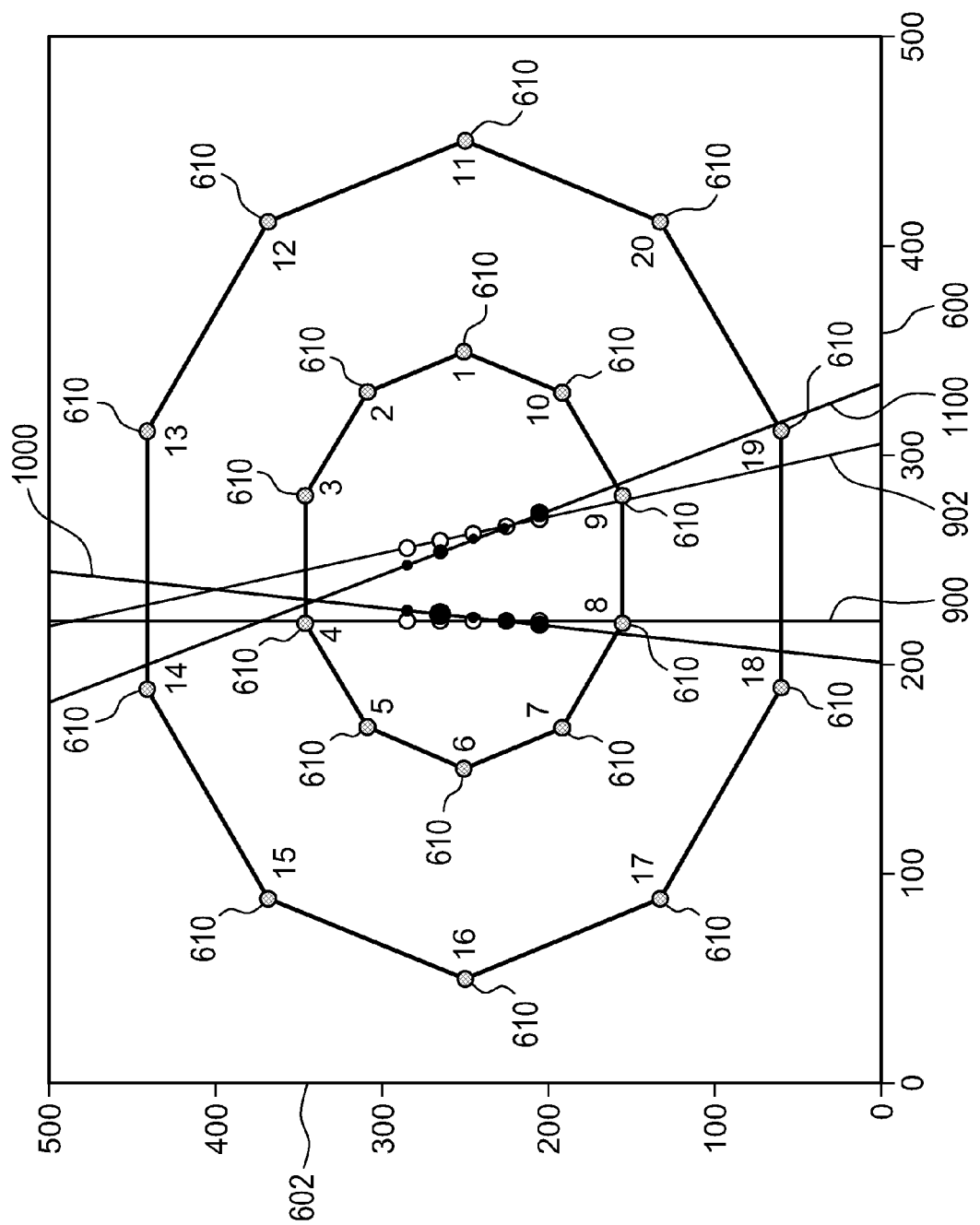

FIG. 11 illustrates how a method according to an embodiment of the invention can be used to compensate for the misaligned catheter 1000. FIG. 11 is identical to FIG. 10 except an online optimization has been performed to find a modified position for the second catheter 1100. The dwell times have also been recalculated. The time at several dwell points has been increased and others have been decreased for both catheters 1000, 1100.

Figure 12:
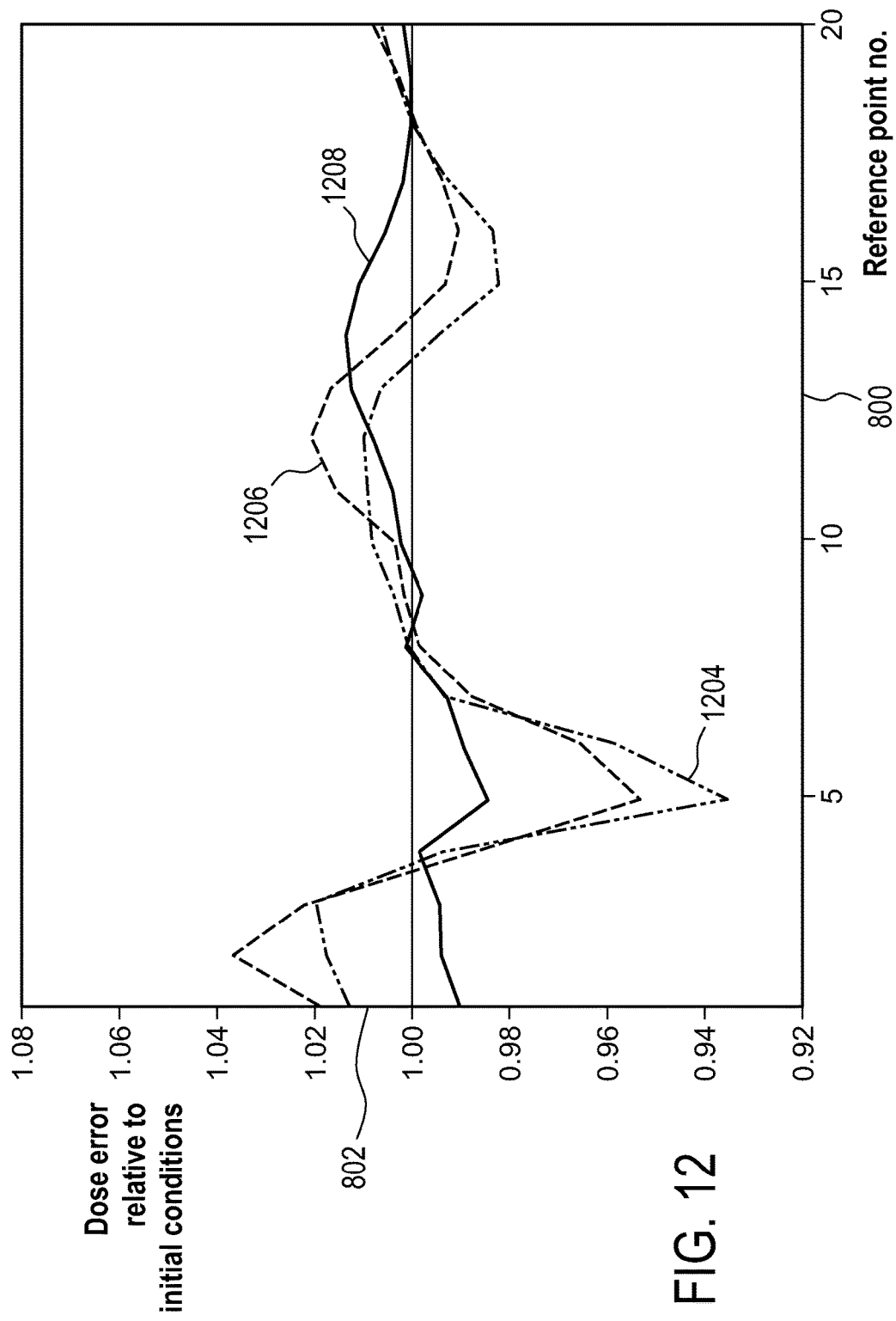
FIG. 12 illustrates the benefit of applying a method according to an embodiment of the invention to the misplaced catheter in FIG. 10.

FIG. 12 is similar to FIG. 8 in that it shows the benefit of applying the method to a situation illustrated by FIGS. 9-11. Again the relative dose air 802 is shown for each of the reference points labeled 1-20 800. The curve labeled 1204 shows the effect of using catheter positions 1000 and 902 without correcting the dwell times. The curve labeled 1206 shows the effect of correcting only the dwell times. Finally curve 1208 shows the effect of correcting the dwell times and using the catheter positions 1000 and 1100. It can be seen that using both corrections as shown in 1208 reduce the dose relative air.

Embodiment of the invention may provide for a method in which, if a treatment plan is to be followed over two or more treatment sessions, it is vital that catheters do not move between the sessions. Otherwise the calculated dose distribution will be invalid and a treatment according to plan can result in insufficient dose deposition within the tumor volume and in damage of surrounding sensitive tissue. In many cases it is not feasible to acquire additional MR images for verification prior to each treatment session. The verification scheme described in the following does not rely on medical imaging, but employs a method of mutual distance determination performed by sensors attached directly to the catheters.

Figure 13:
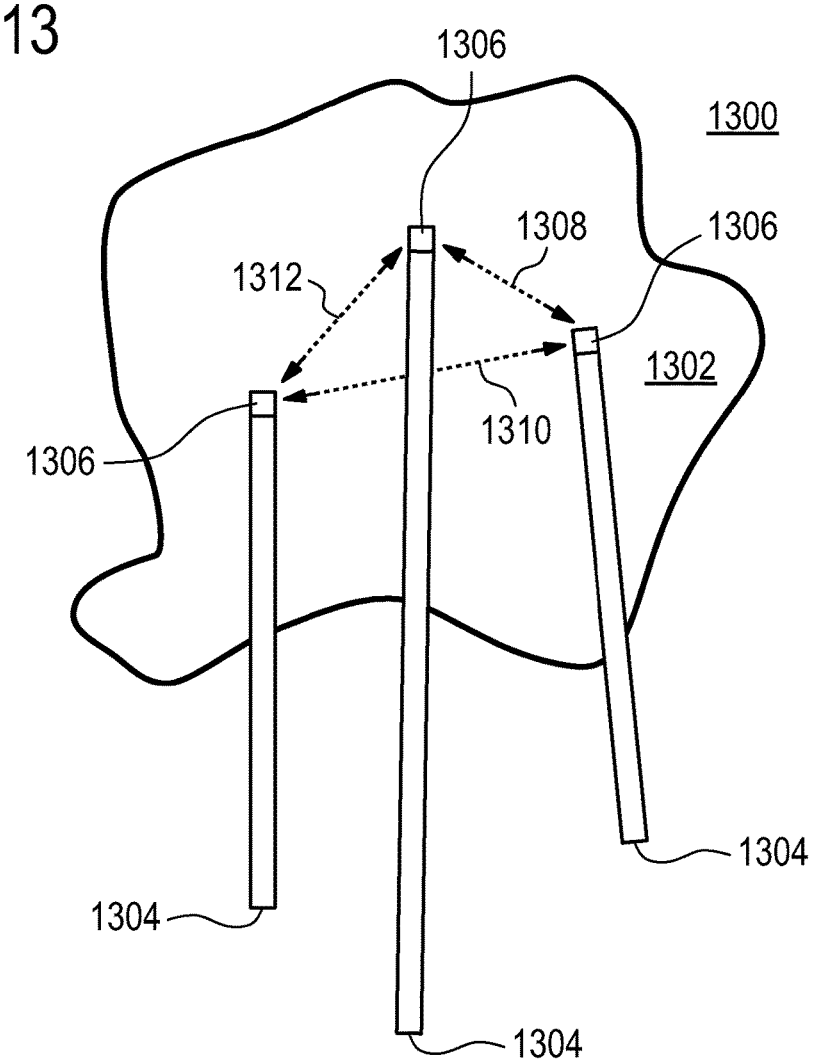
FIG. 13 illustrates the functioning of a catheter location verification system according to an embodiment of the invention.

FIG. 13 illustrates the functioning of a catheter location verification system according to an embodiment of the invention. In FIG. 13 a tumor volume 1302 is surrounded by healthy tissue 1300. Three catheters 1304 have been inserted through the healthy tissue 1300 into the tumor volume 1302. At the tip of each catheter 1304 is a piezoceramic transducer 1306. The piezoceramic transducer is adapted for both sending and receiving ultrasonic signals. In this example each catheter 1304 can emit a piezoelectric signal and the other two remaining catheters 1304 can receive the signal. The delay between the sending and the receiving of the ultrasonic signal or the phase difference of transmitted and received signal may be used to determine a relative distance between each of the tips. Using this method three different distances may be established. Distance labeled 1308, 1310 and 1312. If one of the catheters moves then two of these distances may change. Although the absolute position of the catheters relative to the anatomy of the subject is unknown the relative position between the catheter tips is determined by these three distances 1308, 1310, 1312. Thus if one or more of these probe tips move this may be indicated in a change in one or more of these distances. If the distances change by more than a predetermined amount the subject can be place back into a magnetic resonance imaging system where the location of the catheters relative to the patient anatomy can be determined in absolute terms and the catheter placement positions measured can be used to recalculate catheter control commands.

In FIG. 13, the catheter tip positions are measured using small piezoelectric elements introduced into or integrated with the catheters and connected to the outside via a thin MR-compatible cable along the catheter tube. The relative distance between any two tips can now be determined by measuring the sound propagation time in the tumor volume. An ultrasound wave is emitted by one of the piezoelectric transducers and received by all the other transducers. An external electronic circuit measures the time between emission and reception of the signal or the phase difference of the emitted and received signals. Then the next catheter is used as transmitter and so forth. In this way a complete matrix of sound propagation delays, i.e., distances between the catheter tips is determined. In general, measuring the phase shift of a sine wave is probably more reliable than measuring the pulse propagation time. Such a measurement can be taken over many oscillation periods to increase accuracy and a lock-in detector technique can be used to measure even very small signal amplitudes. Assuming an ultrasound frequency of 100 kHz, the wavelength in water is approximately 15 mm. Relative spatial shifts of the catheters in the mm range can thus easily be detected.

In FIG. 13 the positions of the catheters can be verified using small piezoelectric elements are positioned at the tip of the catheters. In another embodiment they are integrated with the catheters at the catheter tips. In this, case an MR-compatible wiring along the catheter allows the transducers to be contacted from the outside without compromising MR safety. One after the other, the piezo transducers emit an ultrasound wave which is received by all other transducers. The propagation time of the sound (or the phase difference between emitted and received signals) is measured. In this way, the distances between any two catheter tips can be determined very precisely.

A first reference measurement of the distances is taken directly after the insertion of the catheters, ideally while the patient is still under real-time MR observance, to make sure that the positions are correct. At the beginning of each treatment session, the relative positions of the catheter tips are verified by comparing a distance measurement to the initially taken values.

The method for catheter position verification disclosed here relies on miniature piezoceramic ultrasound transducers. Similar, however much more sophisticated, devices are already available for medical applications; they are currently used for intravascular ultrasound imaging (IVUS) and intracardiac imaging. Hollow sphere transducers seem to be particularly well suited for the application described here because of their spherically symmetric radiation pattern. This type of piezoceramics has also been proposed for medical applications, such as high-intensity ultrasound exposimetry and tissue ablation.

Real-time catheter position measurement can be employed to move the patient into the correct position, such that the catheters are well aligned. Additional information about the motion of organs (e.g., simulation of bladder filling/emptying) can be included in the determination of catheter misalignment.

In one embodiment, the pre-interventional planning software suggests not only the optimum, but a number of good solutions for catheter placement. Since the constraints for catheter placement are sometimes difficult to define, it may be easier and less time-consuming for the physician to choose one out of a few good suggestions, instead of trying to adapt the constraint definitions.

In one embodiment, the HDR treatment is performed using miniature X-ray sources instead of radioactive sources (like the ones manufactured by Xoft Inc.). This eliminates the need for a radiation-shielded environment ("bunker") and allows the treatment sessions to take place near or inside an MR scanner. In this way, verification of the catheter positions can easily be done using MR imaging. Furthermore, the complete treatment process could be carried out during real-time MR imaging to verify the exact position of the seed within the catheters.

One embodiment of the catheter position verification based on sound propagation employs additional piezoelectric elements attached to the side of the catheters. In this way not only the tip positions but the also the angular arrangement of the catheters can be verified.

In another embodiment, the ultrasound transducers are not fixed to the catheter tips but can be temporarily inserted from the outside, similar to the radioactive seeds. The sound transducers are shifted right through the open tip of the catheters in order to ensure a good of the emitted sound to the tissue. A mechanical stop at the catheter tip ensures reproducible alignment of the transducers.

In one embodiment, movable ultrasound transducers are inserted in the catheters and distance measurements are performed continuously or stepwise while pulling the transducers along the catheters at constant speed (this can be ensured by a mechanical connection of wires pulling the transducers). In this way not only the tip position, but the complete catheter path can be verified, provided that a sufficiently localized coupling of the sound to the surrounding tissue is possible.

One embodiment includes a stiff mechanical connection of the distal ends of the catheters outside the body. Combined with the distance measurement of the tips this measure ensures correct angulation of the catheters.

One embodiment of the catheter placement verification employs an optical shape sensing device, i.e. an optical fiber using reflectometry to determine its own shape and position. Such a technique is e.g. provided by Luna Technologies. A shape-sensitive fiber can be inserted into the catheters one after the other to precisely determine the position of the catheter tip and the bending of the catheter. If the distal ends of all catheters are rigidly connected, the relative position of all catheters can be determined in this way.

In one embodiment, shape-sensing optical fibers are permanent parts of the catheters. In addition to the above-mentioned position verification, the fibers can be used for real-time position determination during the intervention.

In one embodiment, mapping of the planning image and the real-time images is performed manually by the interventionalist. The proposed needle path is displayed on the planning image only. The physician uses this information to steer the needle in the real-time images. When the needle is in place, the physician determines deviations from the proposed needle path by comparing the images and marks the actual needle position on the planning image. The software then uses this information to calculate the optimization suggestions. This may be the method of choice if automatic image mapping is impossible because of motion or lack of structure in the image.

In one embodiment, the dynamics of respiratory motion is taken into account for automatic mapping of the planning image and the real-time images. This requires the acquisition of additional information about the motion. This can be achieved using external breathing state measurement devices or shape-sensing fibers fixed to the catheters.

In one embodiment, shape-sensing fibers permanently attached to the catheters are used to determine the motion and position of the catheters in real time during the treatment session. An additional real-time optimization algorithm can be employed to induce slight variations of the position of the seed during application in order to compensate for motion of critical organs with respect to the seed due to breathing.

In one embodiment of the simplified optimization algorithm, the dose deviations are expressed as quotients instead of differences:

$$\min\left[\sum_i \left(1 - \frac{d_i^{(1)}}{d_i^{(0)}}\right)^2\right]$$

Another embodiment of the algorithm takes additional boundary conditions for the allowed doses, expressed in terms of inequalities, into account.

A method according to an embodiment or which may be incorporated into a method according to an embodiment of the invention is:
1. A planning MR scan is produced to visualize the lesion and the surrounding tissue/organs in three dimensions
2. The radiologist specifies the treatment volume and the radiation dose to be applied, and delineates the surrounding organs at risk with corresponding limits of the radiation dose
3. The treatment planning software suggests the optimal placement of catheters and dwell positions of HDR brachytherapy sources, optimizing for smallest number of required catheters and best dose distribution
4. In an MR-guided intervention, the needles are placed by the interventionalist. The calculated needle path is overlaid on the real-time MR images to help the physician find the optimum position.
5. After each needle placement, the final needle position is determined from the MR images treatment plan is recalculated using the already inserted needles as fixed parameters. In this way, small corrections of the optimal placement of the next needle can be taken into account.
6. After the intervention, the relative positions of the catheters are measured using the piezoelectric transducers. Then the final treatment plan is calculated with conventional planning software and approved by a radiologist
7. Treatment sessions are carried out. Before each session, the correct position of the catheters is verified. The catheter position may be corrected under guidance of real-time catheter position measurement by moving the patient. Simulations of the motion of organs, such as bladder filling/emptying, can be taken into account. If a misalignment cannot be corrected, a new treatment plan may have to be set up based on a new set of MR images.

Cancer treatment using brachytherapy involves the insertion of the radioactive source seeds into a target region (i.e. tumor). Precise application of the radiation dose is an essential requirement to destroy the malignant while sparing healthy tissue. Currently used seeds possess a rotation-symmetric design and consequently a roughly radial-symmetric radiation/dose distribution. Due to the proximity of target regions and organs at risk a local and properly directed irradiation is essential. The proposed design allows irradiating the target while "shielding" organs at risk and results in a significantly improved dose distribution.

In one embodiment of the invention the radiation sources are not rotation-symmetric in design and allow a conformal (adapted anisotropic) dose distribution.

A workflow according to an embodiment of the invention includes a combination of image-based dose and source placement planning as well as angular applicator control/image guidance during insertion. This approach may allow a higher placement accuracy with locally increased dose, reduced irradiation of organs at risk enabling reduced adverse side-effects, improved cure-rates and a more efficient clinical workflow.

Brachytherapy involves placing numerous radiation sources (seeds) into a target region (tumor). Depending on the appropriateness criteria low, medium or high dose brachy-therapy can be used for treatment (Low Dose Rate (LDR), Medium Dose Rate (MDR), High Dose Rate (HDR)).

During the HDR treatment a computer-controlled machine (after-loader) pushes a single highly radioactive seed into previously placed catheters or needles one by one for a variable (dose planned) duration. HDR is normally applied in several treatment sessions over 2-5 consecutive days (HDR mono-therapy) instead of more highly fractionated application of typically 5-7 weeks for external beam radiation, or it is used as an add-on to shorten the external beam radiation protocol in combination therapy.

Success of these types of procedures may require accurate dose delivery to a target volume according to a pre-procedural plan, and this is confounded by inaccurate placement and/or dwell times of the brachytherapy seeds.

Precise application of dose to the target region (tumor) and sparing of surrounding tissue (organs at risk) is an essential prerequisite to enable higher treatment doses, shorter treatment times, reduced adverse side-effects, improved cure-rates and a consequently a more efficient clinical workflow.

Figure 14:
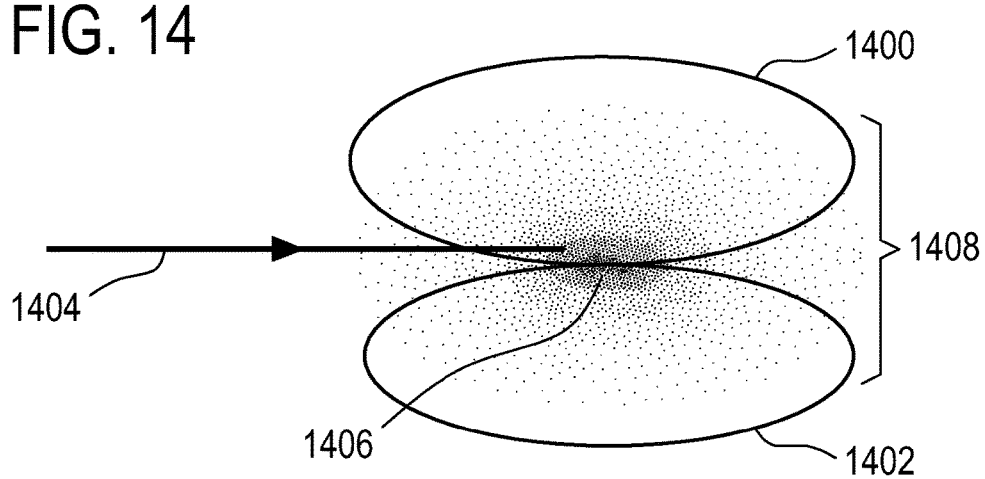
FIG. 14 illustrates a radiation field from an isotropic radiation source.

FIG. 14 illustrates why it may be beneficial to use a brachytherapy radiation source with an anisotropic radiation source. Region 1400 is a targeted region. The targeted region 1400 may for instance represent a tumor. Region 1402 below region 1400 is identified as an organ or a region at risk. For instance this may be an organ which would not be beneficial to irradiate at the same time that the targeted region 1400 is eradiated. 1404 shows an access path between the targeted region 1400 and the organ at risk 1402. The access path 1404 for instance may be provided by a brachytherapy catheter. The point 1406 illustrates the location of an isotropic radiation source. The isotropic radiation source 1406 produces an isotropic radiation field 1408. The production of an isotropic radiation field 1408 is not beneficial because both the target region 1400 and the organ at risk 1402 are eradiated. Therefore it may be beneficial to have a radiation source which is anisotropic so that radiation may be preferentially directed into the target region 1400 and not into the organ at risk 1402.

The current radial symmetric design of sources, as illustrated in FIG. 14, limits the degree of freedom in dose distribution significantly. Since the number of feasible access paths 1404 for seed placement 1406 is often anatomically limited and the boundary surfaces between target region and surrounding tissue can be very close, the dose distribution 1408 of currently employed seeds is not always adequate. If the seed is centered at the boundary of target 1400 and organ at risk 1402 the boundary of the target is treated well but the organ at risk gets a too high dose. If the access path is vertically moved up to spare the organ at risk only a low dose reaches the outer rim of the target. This restriction by design leads to an undesirable compromise between radical treatment and sparing of organs at risk.

The dose distribution of seeds as used today may be radially quite non-uniform. This variation between different seeds adds an additional uncertainty about the true applied dose distribution.

Radiation sources (seed) according to some embodiments of the invention have a non-rotational-symmetric dose distribution by design allowing an anisotropic radiation pattern. Via selecting seeds with appropriate irradiation angles and controlled angulation/rotation of the radiation source an improved conformal dose distribution can be obtained.

To alleviate the application procedure a workflow including image-based dose/placement planning in conjunction with computer-controlled seed placement and optional image-based seed tracking is proposed which allows efficient high-accuracy dose application and treatment.

Figure 15:
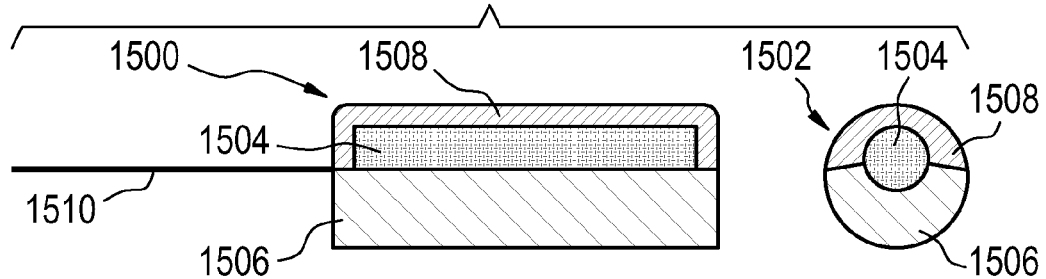
FIG. 15 illustrates a radiation source or seed according to an embodiment of the invention.

FIG. 15 shows an example of an anisotropic radiation source for brachytherapy according to an embodiment of the invention. There is a cross-sectional side view of a radioactive seed 1500 and a cross-sectional axial view of the same radioactive seed shown. On the top half there is a radioactive substance 1504 with the bottom hemisphere being comprised of a shield material 1506. An unshielded region or material 1508 covers the radioactive substance 1504. The use of the shield material 1506 causes an anisotropic radiation distribution around the radioactive seed 1500, 1502. There is a seed control wire 1510 which allows the radioactive seed 1500, 1502 to be inserted into a brachytherapy catheter and also to be rotated. Rotating the radioactive seed allows control of the anisotropic radiation field that it generates.

Figure 16:
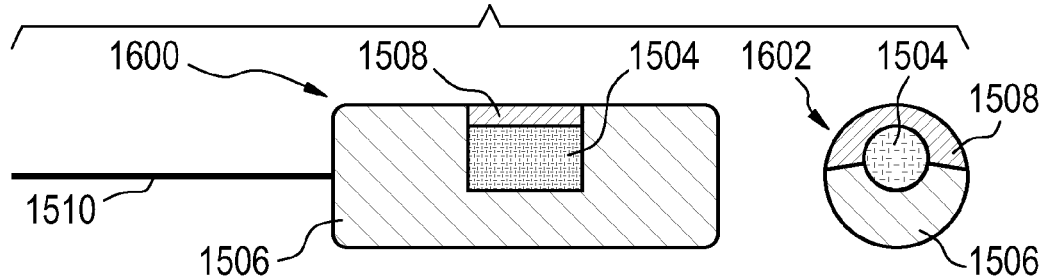
FIG. 16 illustrates a radiation source or seed according to a further embodiment of the invention.

FIG. 16 shows another embodiment of an anisotropic radiation source according to an embodiment of the invention. Again there is a cross-sectional side view 1600 and a cross-section axial view 1602 of the radioactive seed or source. The embodiment shown in FIG. 16 is similar to that of FIG. 15 except along the axial direction the radioactive substance 1504 is shorter. This causes an axially shortened irradiation field.

Figure 17:
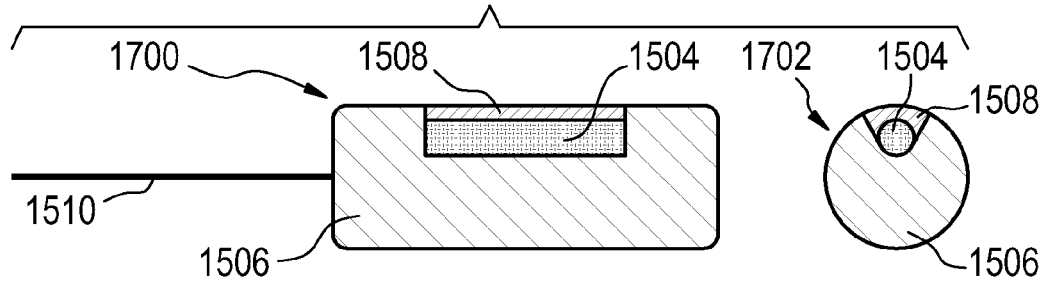
FIG. 17 illustrates a radiation source or seed according to a further embodiment of the invention.

FIG. 17 shows a further embodiment of an anisotropic radiation source according to an embodiment of the invention. This embodiment is similar to the embodiment shown in FIGS. 15 and 16 except in this case the radioactive material is smaller and further away from the access of the seed control wire 1510. This causes a radially focused irradiation field.

Figure 18:
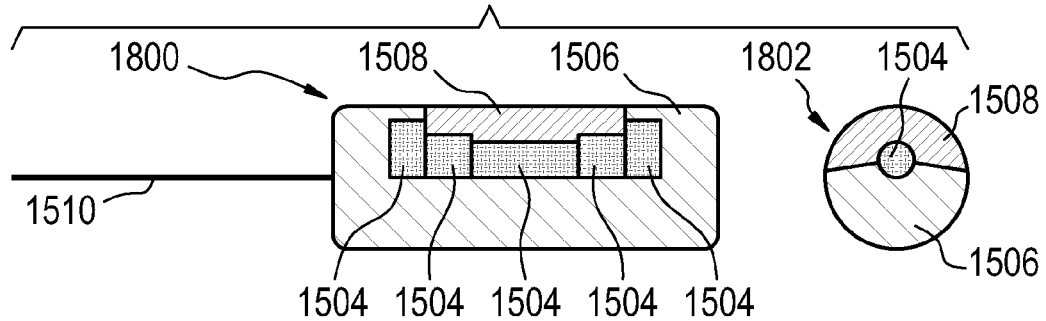
FIG. 18 illustrates a radiation source or seed according to a further embodiment of the invention.

FIG. 18 shows a further embodiment of an anisotropic radiation source according to an embodiment of the invention. In this embodiment the radioactive material is treated such that it creates an axially homogenized irradiation field. At different positions along the axial direction there are different amounts of radioactive material.

In FIGS. 15 to 18 various radiation seeds are illustrated. Considering the access path situation from FIG. 14 it is clear that the anisotropic dose distribution allows higher doses for the target region while "shielding" the organs at risk when being inserted with the shield pointing downwards.

Various Nucleotides 1504 may be used for constructing anisotropic radiation sources, some examples are, but not limited to:

| Radionuclide | Type | Half-life | Energy |
| --- | --- | --- | --- |
| Caesium-137 ($^{137}$Cs) | γ-ray | 30.17 years | 0.662 MeV |
| Cobalt-60 ($^{60}$Co) | γ-rays | 5.26 years | 1.17, 1.33 MeV |
| Iridium-192 ($^{192}$Ir) | β$^-$-particles | 73.8 days | 0.38 MeV (mean) |
| Iodine-125 ($^{125}$I) | γ-rays | 59.6 days | 27.4, 31.4 and 35.5 keV |
| Palladium-103 ($^{103}$Pd) | γ-ray | 17.0 days | 21 keV (mean) |
| Ruthenium-106 ($^{106}$Ru) | β$^-$-particles | 1.02 years | 3.54 MeV |

Examples of possible shield materials 1506 are, but not limited to: Lead, Barium sulfate, and Steel.

Figure 19:
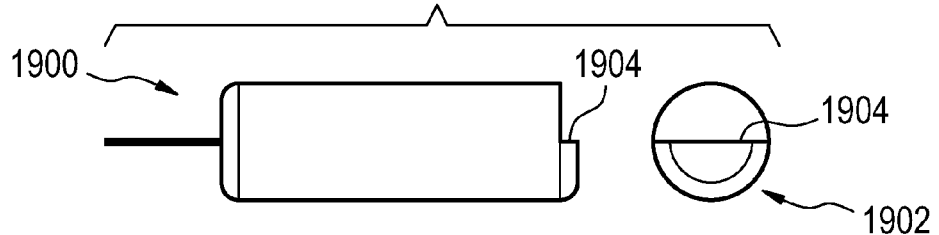
FIG. 19 illustrates a radiation source or seed according to a further embodiment of the invention.
Figure 20:
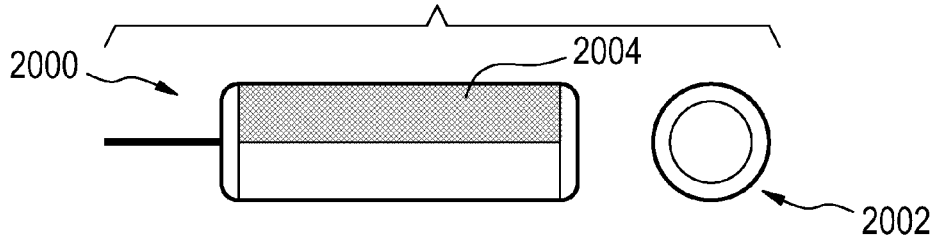
FIG. 20 illustrates a radiation source or seed according to a further embodiment of the invention.
Figure 21:
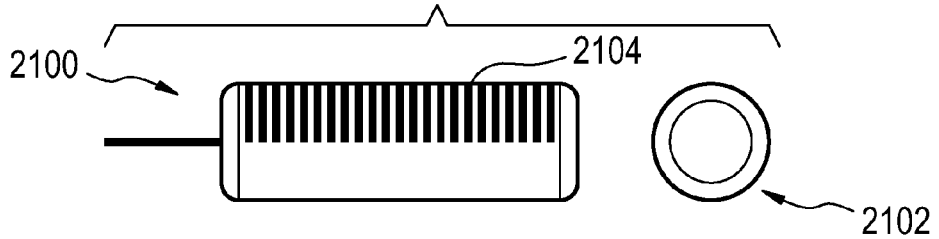
FIG. 21 illustrates a radiation source or seed according to a further embodiment of the invention.

To achieve a correct angulation of the marker during application a directional marking is essential. In FIGS. 19, 20, and 21 some possible embodiments of respective seed shell designs are shown.

FIG. 19 shows a side view 1900 and an axial view 1902 of a radioactive seed according to a further embodiment of the invention. The radioactive seed in FIG. 19 is an anisotropic radiation field. So that it can be understood in which direction the field is produced there is a notch 1904 on the end of the radioactive seed or source.

FIG. 20 shows a further embodiment of a radioactive seed or source according to an embodiment of the invention. There is a side view 2000 and an axial view 2002 shown. To indicate the direction of the anisotropic radiation field a pattern 2004 or a painted surface is used to indicate the axial asymmetry of the radioactive seed.

FIG. 21 shows a further embodiment of a radioactive seed or source according to an embodiment of the invention. A side view 2100 and an axial view 2102 is shown. In this embodiment there is a grooved surface 2104. Grooves could be in the unshielded coating material or may also include a grooved substance and/or shielding material. The embodiments shown in FIGS. 19-21 enable the determination of the direction of the anisotropic radiation field. In yet another embodiment a fiduciary marker may be mounted on the radiation shield so that the direction or orientation of the radioactive seed may be determined using magnetic resonance imaging.

The angular surface coloring and grooves principle can also be extended to a more advanced pattern (i.e. bar code) to identify the seed type along with its orientation. Similar orientation/identification designs could also be placed on the attached seed control wire to simplify the design of the source itself.

It is also possible to measure the actual dose distribution (measure the anisotropic dose distribution) of the seed right before the treatment inside the applicator and adjust the treatment plan accordingly.

Additionally it is possible to incorporate an imaging marker into the design. This feature would allow real-time tracking and validation of the marker position/orientation.

Figure 22:
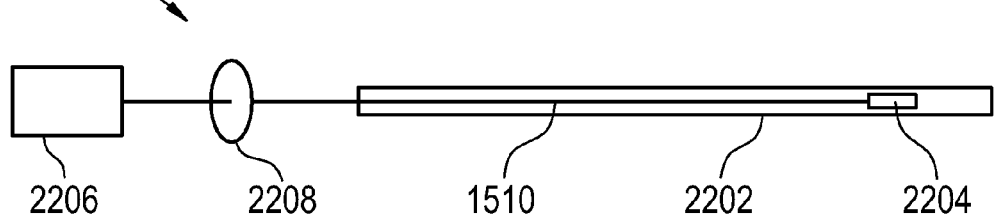
FIG. 22 illustrates a brachytherapy catheter according to an embodiment of the invention.

In FIG. 22 a schematic sketch of the applicator and control-device is shown. FIG. 22 shows a brachytherapy catheter 2200 according to an embodiment of the invention. The brachytherapy catheter comprises a seed guide 2202. The seed guide is the catheter tube inserted into a subject. There is then a radioactive seed or source 2204 connected to a seed control wire 1510. This wire 1510 enables the radioactive seed 2204 to be inserted or removed from the seed guide 2202. Further it also enables the rotational orientation of the radioactive seed 2204 to be controlled. The position and rotational orientation of the radioactive seed 2204 within the seed guide 2202 can be controlled as a function of time.

The seed control wire 1510 is connected to an axial position sensing movement and control device 2206 and a radial position sensing and rotational control device 2208. This enables the radioactive seed 2204 to be rotated and also to be moved in and out of the seed guide tube 2202. In an alternative embodiment the radial position sensing and rotational control device 2208 is absent. This would be useful for instance when the radioactive seed 2204 produces an isotropic radiation field. Such a brachytherapy catheter 2202 could also be controlled manually. The seed control wire 1510 could have a device which controls its depth and also an indicator which indicates the rotational orientation of the radioactive seed 2204.

Figure 23:
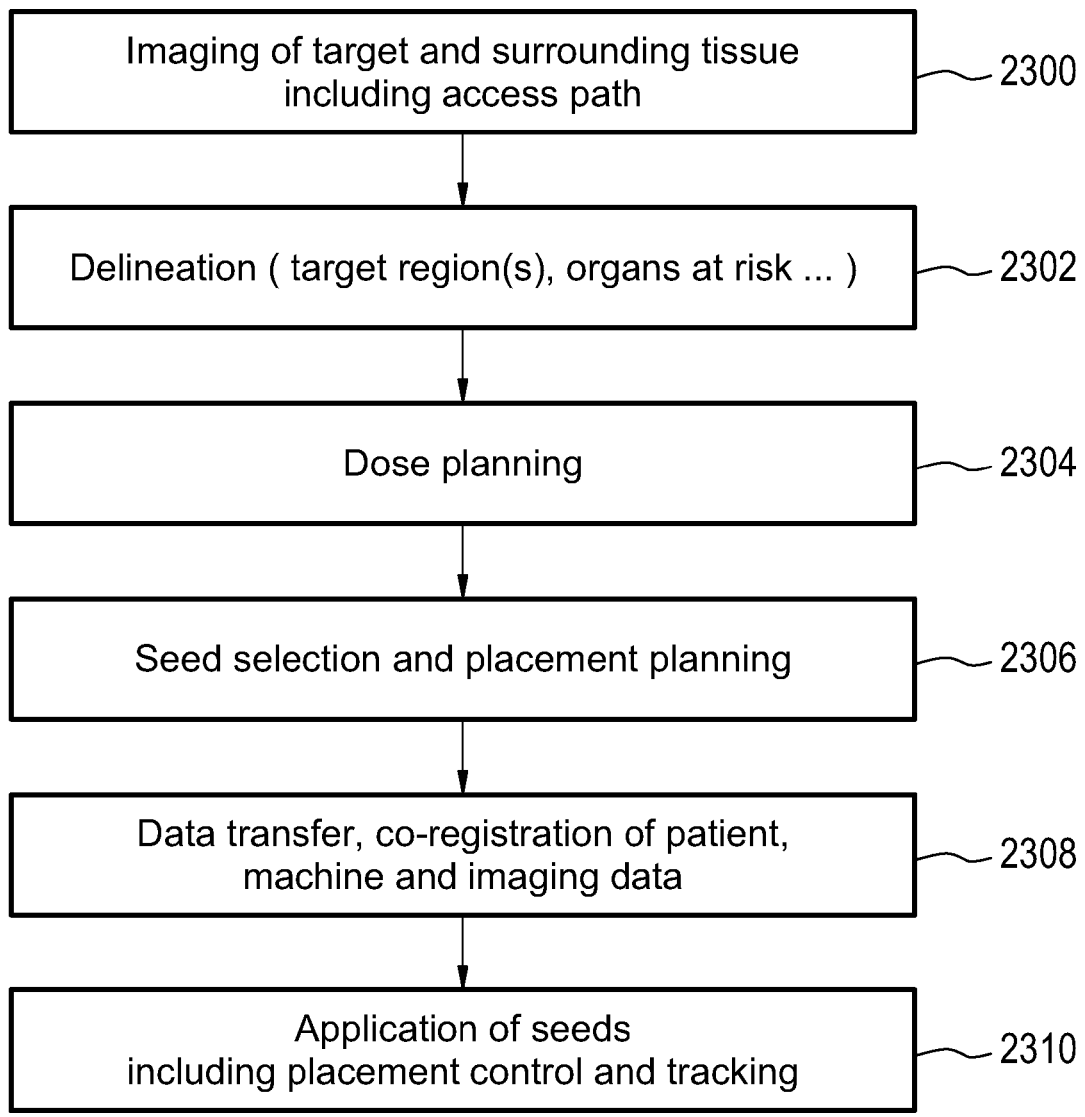
FIG. 23 shows a flow diagram which illustrates a method according to a further embodiment of the invention.

FIG. 23 shows a method according to an embodiment of the invention. First in step 2300 imaging the target and surrounding tissue including an access path is performed. This is performed with step 100 of FIG. 1. Next in step 2302 the delineation of target regions and organs at risk is determined. Next in step 2304 dose planning is performed. Next in step 2306 radioactive seed selection and placement planning is performed. Radioactive seeds of different strengths and types of radioactive seeds may be selected. For instance seeds which produce isotropic radiation fields and/ or seeds which produce anisotropic radiation fields may be selected. Next in step 2308 there is data transfer co-registration of the patient and machine and image data is performed. Finally in step 2310 the seeds are applied to the subject. This includes placement control and tracking of the radioactive seeds. For instance, in some embodiments magnetic resonance imaging may be used to track the location of the radioactive seeds and/or determine their rotational orientation. The steps in FIG. 1 may be combined with those steps shown in FIG. 23. The steps in FIG. 23 are particularly oriented towards use of a radioactive seed with an anisotropic radiation source. In some instances the method shown in FIG. 23 may be performed independently of the steps shown in FIG. 1.

To use an embodiment of the invention efficiently a workflow as shown in FIG. 23 is suggested. First imaging of the target region(s) is done. Based on this data delineation of target and organs at risk or other structures which are relevant for dose planning is performed. Thereafter, dose planning, taking into account the additional degrees of freedom provided by anisotropic dose patterns, can be carried out.

The calculated result provides information about the placement including rotation of the respective seed types and their application duration. During the intervention this data is spatially co-registered with the patient space and the applicator device which then places the seeds according to the planning data.

Depending on the applicator type (e.g. rigid needles or flexible catheters) control of the precise localization and orientation can be done differently.

For rigid applicators a precise mechanical design and motorized seed control loop provide inherent localization accuracy.

For flexible applicators the precise placement can be monitored using real-time imaging (e.g. US, MR). This would also allow a more advanced workflow which involves a potential real-time re-planning of seed placement depending on the respective true applicator and organ positions. This tracking could also be achieved using shape sensing applicator tubes. Applicator shape and therefore trajectory information can also be obtained from image data acquired after applicator but before seed placement (magnetic resonance imaging, computed tomography, ultrasound, and X-ray). Given the shape of the applicator using any of the above methods, the orientation of the seed can be calculated depending on the orientation of the proximal end of the seed control wire by means of a mechanical model of the seed control wire.

In an embodiment for LDR, the seeds are made of oval (or any other non-radially symmetric) shape to prevent rotation of the seed after placement, which may otherwise occur due to physiological motion. Alternatively, the seeds may be equipped with hooks, hinges that fixate to the tissue upon release from the needle/catheter.

Some embodiments of the invention may have the following features:
1) Design of brachytherapy seed with determinate anisotropic radiation pattern (radial and/or axial asymmetry).
2) Controlled angular positioning of seed during placement and treatment.
3) Design feature (marker) allow determining the radial orientation of the seed.
4) Treatment planning procedure involving seeds with various radiation patterns, rotations, and movement regimes.
5) Measurement of actual dose distribution for adaptive treatment planning.
6) Imaging of target regions and respective re-planning of treatment.
7) Placement of above seed with rigid applicators and control mechanism.
8) Placement of above seed under image guidance.
9) Placement of above seed using shape sensing applicators.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 medical apparatus
202 magnetic resonance imaging system
204 magnet
206 open space
208 imaging zone
210 subject
212 subject support
214 gradient coils
216 gradient coil power supply
218 radio frequency coil
220 transceiver
222 catheter
224 computer
226 hardware interface
228 processor
230 user interface
232 computer storage
234 computer memory
240 brachytherapy treatment plan
242 pulse sequence
244 planning magnetic resonance data
246 catheter placement positions
248 catheter control commands
250 guidance magnetic resonance data
252 magnetic resonance image
254 image segmentation
260 control module
262 image reconstruction module
264 image segmentation module
266 catheter placement items and control command generation module
268 graphical user interface driver module
270 graphical user interface
274 treatment zone
276 catheter placement position
278 catheter inserted button
300 medical apparatus
302 catheter actuator
400 medical apparatus
402 catheter location verification system
404 measured catheter position
406 catheter location verification system driver
500 magnetic resonance image
501 graphical user interface
502 first catheter placement position
504 second catheter placement position
506 catheter
508 identification number
600 first directional dimension in arbitrary units
602 second directional dimension in arbitrary units
604 first brachytherapy radiation source
606 second brachytherapy radiation source
608 third brachytherapy radiation source
610 reference points
704 first brachytherapy radiation source
706 second brachytherapy radiation source
708 third brachytherapy radiation source
800 reference point number
802 relative dose error
804 without correction
806 with dwell times corrected
808 with dwell times and positions corrected
900 first catheter placement position
902 second catheter placement position
904 dwell location of first radiation source
906 dwell location of second radiation source
1204 without correction
1206 with dwell times corrected
1208 with dwell times and positions corrected
1300 healthy tissue
1302 tumor volume
1304 catheter
1306 piezoceramic transducer
1308 first distance
1310 second distance
1312 third distance
1400 target region
1402 organ at risk
1404 access path
1406 radiation source
1408 isotropic radiation field
1500 cross-sectional side view of radioactive seed
1502 cross-sectional axial view of radioactive seed
1504 radioactive substance
1506 shield material
1508 unshielded region
1510 seed control wire
1600 cross-sectional side view of radioactive seed
1602 cross-sectional axial view of radioactive seed
1700 cross-sectional side view of radioactive seed
1702 cross-sectional axial view of radioactive seed
1800 cross-sectional side view of radioactive seed
1802 cross-sectional axial view of radioactive seed
1900 side view of radioactive seed
1902 axial view of radioactive seed
1904 notch
2000 side view of radioactive seed
2002 axial view of radioactive seed
2004 patterned surface
2100 side view of radioactive seed
2102 axial view of radioactive seed
2104 grooved surface
2200 brachytherapy catheter
2202 seed guide
2204 radioactive seed or source
2206 axial position sensing and movement control
2208 radial position sensing and rotation control

The invention claimed is:

1. A medical apparatus (200, 300, 400) comprising:
   A magnetic resonance imaging system (202) for acquiring magnetic resonance data (244, 250) from an imaging zone (208);
   a display (270, 501) for displaying images (252, 500);
   a processor (228) for controlling the medical apparatus;
   a memory (234) for storing machine executable instructions for execution by the processor, wherein execution of the instructions causes the processor to receive a brachytherapy treatment plan (240) for treating a subject (210), wherein execution of the instructions further causes the processor to acquire (100) planning magnetic resonance data (244) using the magnetic resonance imaging system, wherein execution of the instructions further causes the processor to calculate (102) a catheter placement position (246, 900, 902) and a catheter control command (248) for each of the multiple brachytherapy catheters using the brachytherapy treatment plan and the planning magnetic resonance data, wherein the catheter control command is descriptive of locations and dwell times for the locations for one of the multiple brachytherapy catheters, wherein execution of the instructions causes the processor, for each catheter placement position, to repeatedly:
acquire (106) guidance magnetic resonance data (250);
reconstruct (108) an image (252, 500) from the guidance magnetic resonance data;
display (110) the image on the display;
display (112) the catheter placement position on the image;
receive (114) a catheter inserted signal from a user interface;
segment (116) the image to determine the catheter placement position after receiving the catheter inserted signal;
recalculate (116) the catheter placement positions for each remaining catheter placement position after receiving the catheter inserted signal; and
recalculate (116) the catheter control command for the multiple catheters after receiving the catheter inserted signal.

2. The medical apparatus of claim 1, wherein at least one of the multiple brachytherapy catheters (1500, 1600, 1700, 1800) is configured for generating an anisotropic radiation field, wherein the catheter control command is further descriptive of a rotational position of the anisotropic radiation field of the brachytherapy catheter for each of the dwell times.

3. The medical apparatus of claim 2, wherein the medical apparatus further comprises a catheter actuator (302, 2206, 2208) configured for controlling the position and the rotational position of the anisotropic radiation field of each of the multiple brachytherapy catheters as a function of time, wherein execution of the instructions further causes the processor to control the position of the multiple brachytherapy catheters as a function of time with the catheter actuator in accordance with the catheter control commands.

4. The medical apparatus of claim 2, wherein the at least one of the multiple brachytherapy catheters comprises an anisotropic radiation source for generating the anisotropic radiation field with a radial and/or axial asymmetry.

5. The medical apparatus of claim 2, wherein the at least one brachytherapy catheter comprises a magnetic resonance positional marker descriptive of the rotational position of the anisotropic radiation field, wherein execution of the instructions further cause the processor to determine a current rotational position of the anisotropic radiation field by identifying an orientation of the positional marker in the guidance magnetic resonance data, and wherein the catheter control commands are generated in accordance with the current rotation position.

6. The medical apparatus of claim 1, wherein the medical apparatus further comprises a catheter location verification system (402) configured for measuring a catheter position for each of the of the multiple brachytherapy catheters, wherein execution of the instructions further cause the processor to measure the catheter position for each of the multiple brachytherapy catheters after receiving the catheter inserted signal for all of the multiple brachytherapy catheters using the location verification system.

7. The medical apparatus of claim 6, wherein execution of the instructions further cause the processor to:
measure a repeat catheter position (1306, 1308, 1310) for each of the multiple brachytherapy catheters after receiving the catheter inserted signal for all of the multiple brachytherapy catheters using the location verification system;
generate a catheter position verified signal if the repeat catheter position of each of the multiple brachytherapy catheters is within a predetermined distance from the catheter position; and
generate a catheter moved signal if the repeat catheter position of each of the multiple brachytherapy catheters is not within a predetermined distance from the catheter position.

8. The medical apparatus of claim 7, wherein execution of the instructions further causes the processor to:
re-acquire the planning magnetic resonance data using the magnetic resonance imaging system if the catheter moved signal is generated;
recalculate the catheter control command for each of the multiple brachytherapy catheters using the brachytherapy treatment plan and the re-acquired planning magnetic resonance data.

9. The medical apparatus of claim 6, wherein each of the multiple brachytherapy catheters comprise a tip, wherein the tip comprises a piezoelectric transducer (1306) for sending and receiving ultrasonic pulses, wherein the catheter location verification system is configured for sending an ultrasonic pulse using the piezoelectric transducer of each of the multiple brachytherapy catheters and receiving the ultrasonic pulse with at least one other of the multiple brachytherapy catheters, wherein execution of the instructions further causes the processor to:
generate the ultrasonic pulse using the piezoelectric transducer of each of the multiple brachytherapy catheters;
receiving the ultrasonic pulse with the at least one other of the multiple brachytherapy catheters;
determining a delay and/or phase shift for the received ultrasonic pulse; and
storing the delay and/or phase shift in the memory as the catheter position.

10. The medical apparatus of claim 6, wherein each of the multiple brachytherapy catheters comprise a shape sensing fiber optic, wherein the catheter location verification system is configured for measuring the catheter position using the shape sensing fiber optic of each of the multiple brachytherapy catheters, wherein execution of the instructions further causes the processor to measure the catheter position using the shape sensing fiber optic of each of the multiple brachytherapy catheters.

11. The medical apparatus of claim 1, wherein execution of the instructions further causes the processor to:
segment the image reconstructed from the guidance magnetic resonance data to identify catheter locations; and
display the catheter locations on the display.

12. The medical apparatus of claim 1, wherein the medical apparatus further comprises a catheter actuator (302, 2206) configured for controlling the position of the multiple brachytherapy catheters as a function of time, wherein execution of the instructions further causes the processor to control the position of the multiple brachytherapy catheters by controlling the catheter actuator in accordance with the catheter control commands.

13. A method of using a medical apparatus (200, 300, 400) for guiding a catheter (222, 506), wherein the medical apparatus comprises a magnetic resonance imaging system (202) for acquiring magnetic resonance data (244, 250) from an imaging zone (208), wherein the medical apparatus further comprises a display (270, 501) for displaying images (252, 500), wherein the method comprises the steps of:
 receiving a brachytherapy treatment plan (240) for treating a subject (210),
 acquiring (100) planning magnetic resonance data using the magnetic resonance imaging system,
 calculating (102) a catheter placement position (246, 900, 902) and a catheter control command for each of the multiple brachytherapy catheters using the brachytherapy treatment plan and the planning magnetic resonance data, wherein the catheter control command is descriptive of locations and dwell times for the locations for the multiple brachytherapy catheters,
wherein the method further comprises repeatedly performing the steps of:
 acquiring (106) guidance magnetic resonance data (250);
 reconstructing (108) an image (252, 500) from the guidance magnetic resonance data;
 displaying (106) the image on the display;
 displaying (112) the catheter placement position on the image;
 receiving (114) a catheter inserted signal from a user interface;
 segmenting (116) the image to determine the catheter placement position after receiving the catheter inserted signal;
 recalculating (116) the catheter placement for each remaining catheter placement position after receiving the catheter inserted signal; and
 recalculating (116) the catheter control command for the multiple catheters after receiving the catheter inserted signal.

14. The method of claim 13, further comprising the steps of:
 inserting one of the multiple brachytherapy catheters into the subject for each catheter placement position; and
 adjusting the catheter placement of the one of the multiple brachytherapy catheters using the catheter placement position on the image.

15. A computer program product comprising machine executable instructions (260, 262, 264, 266, 268) for execution by a processor (228) controlling a medical apparatus (200, 300, 400), wherein the medical apparatus comprises a magnetic resonance imaging system (202) for acquiring magnetic resonance data (244, 250) from an imaging zone (208), wherein the medical apparatus further comprises, a display (252, 501) for displaying images, wherein execution of the instructions causes the processor to receive a brachytherapy treatment plan (240) for treating a subject (210),
 wherein execution of the instructions further causes the processor to acquire (100) planning magnetic resonance data (244) using the magnetic resonance imaging system,
 wherein execution of the instructions further causes the processor to calculate (102) a catheter placement position (246, 900, 902) and a catheter control command (248) for each of the multiple brachytherapy catheters using the brachytherapy treatment plan and the planning magnetic resonance data, wherein the catheter control command is descriptive of locations and dwell times for the locations for at least one of the multiple brachytherapy catheters,
 wherein execution of the instructions causes the processor, for each catheter placement position, to repeatedly:
 acquire (106) guidance magnetic resonance data (250);
 reconstruct (108) an image (252, 500) from the guidance magnetic resonance data;
 display (110) the image on the display;
 display (112) the catheter placement position on the image;
 receive (114) a catheter inserted signal from a user interface;
 segment (116) the image to determine the catheter placement position after receiving the catheter inserted signal;
 recalculate (116) the catheter placement for each remaining catheter placement position after receiving the catheter inserted signal; and
 recalculate (116) the catheter control command for the multiple catheters after receiving the catheter inserted signal.

* * * * *